(12) United States Patent
Kuchta et al.

(10) Patent No.: US 7,045,583 B2
(45) Date of Patent: May 16, 2006

(54) OLEFIN POLYMERIZATION CATALYST SYSTEM

(75) Inventors: Matthew Cornyn Kuchta, Houston, TX (US); Francis Charles Rix, League City, TX (US)

(73) Assignee: Exxon Mobil Chemical Patents Inc., Houston, TX (US)

(*) Notice: Subject to any disclaimer, the term of this patent is extended or adjusted under 35 U.S.C. 154(b) by 0 days.

(21) Appl. No.: 10/744,297

(22) Filed: Dec. 22, 2003

(65) Prior Publication Data

US 2005/0137367 A1    Jun. 23, 2005

(51) Int. Cl.
C08F 4/42 (2006.01)
C08F 4/60 (2006.01)
C08F 4/52 (2006.01)

(52) U.S. Cl. .................. 526/172; 526/161; 556/51; 502/103

(58) Field of Classification Search ............ 526/172, 526/161; 556/51; 502/202, 203
See application file for complete search history.

(56) References Cited

U.S. PATENT DOCUMENTS 6,333,423 B1   12/2001  Kol et al. ............... 556/56
2002/0019503 A1  2/2002  Kol et al. ............... 526/134

FOREIGN PATENT DOCUMENTS

| EP | 0 953 571 | 11/1999 |
|---|---|---|
| JP | 11 080228 A | 3/1999 |
| WO | WO 0069922 A1 | 11/2000 |
| WO | WO 01/18010 A1 * | 3/2001 |
| WO | WO 0118010 A1 | 3/2001 |
| WO | WO 0130860 A1 | 5/2001 |
| WO | WO 0130861 A1 | 5/2001 |
| WO | WO 0236638 A2 | 10/2002 |

OTHER PUBLICATIONS

Organometallics 2000, 19, 5325.
Organometallics 2001, 20, 3560.
Organometallics 2001, 20, 1056.
J.C.S. Chem. Comm. 2000, 379.
JACS 2000, 122, 10706.
J.C.S. Chem Comm. 2001, 2120.
Organometallics 2001, 20, 3017.
Inorganic Chemistry 2001, 40, 4263.
Organometallics 2002, 21, 662.
Organometallics 2002, 21, 1367.
Patent Abstracts of Japan, vol. 1999, No. 08, Jun. 30, 1999, & JP 11 080228 A, Mitsui Chem Inc., Mar. 26, 1999.
Alcazar-Roman et al., "Electronic Influence of Ligand Substituents on the Rate of Polymerization of ε-caprolactone by single-site Aluminum Alkoxide Catalysts", Dalton Trans., (15), 2003, pp. 3082-3087.
Suzuki et al., "Recent Advances in Phenoxy-Based Catalysts for Olefin Polymerization", Bull. Chem. Soc. Jpn., 76, 2003, pp. 1493-1517.

* cited by examiner

Primary Examiner—David W. Wu
Assistant Examiner—Rip A. Lee
(74) Attorney, Agent, or Firm—Catherine L. Bell

(57) ABSTRACT

This invention relates to a catalyst precursor compound comprising a tridentate phenoxy-amide-amine group bound to a group 3 to 12 metal or lanthanide metal. In particular, this invention relates to a catalyst precursor compound represented by the formula:

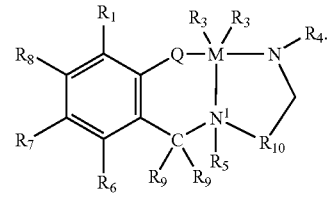

64 Claims, No Drawings

OLEFIN POLYMERIZATION CATALYST SYSTEM

FIELD OF THE INVENTION

This invention relates to a process to polymerize olefins using phenoxy-amide-amine based catalyst precursor compounds and polymers produced therefrom.

BACKGROUND OF THE INVENTION

The technical sphere of olefin polymerization is an area offering many new opportunities to provide new catalysts and catalyst systems to produce new polymers. The following invention relates to new polymerization technology based upon phenoxy-amide-amine catalyst precursor compounds. Other somewhat similar catalyst precursors have been proposed, however none described the phenoxy-amide-amine based catalyst precursor compounds described herein.

Examples of other catalyst precursors include Bis-Amide-Amine ("BAA") group 4 compounds disclosed in: Organometallics 2000, 19, 5325; Organometallics 2001, 20, 3560; Organometallics 2001, 20, 1056; WO 0130861 A1; WO 0130860 A1; and WO 0069922 A1.

Examples of other catalyst precursors include Bis-Phenoxy-Amine ("BPA") group 4 compounds disclosed in: J.C.S. Chem. Comm. 2000, 379; JACS 2000, 122, 10706; JCS Chem. Comm. 2001, 2120; Organometallics 2001, 20, 3017; Inorganic Chemistry 2001, 40, 4263; Organometallics 2002, 21, 662; Organometallics 2002, 21, 1367; WO 0118010A1; WO 0236638A2; US 2002 00119503A1; U.S. Pat. No. 6,333,423.

SUMMARY OF THE INVENTION

This invention relates to a catalyst precursor compound comprising a tridentate phenoxy-amide-amine group bound to a group 3, 4, 5, 6, 7, 8, 9, 10, 11 or 12 metal or a lanthanide metal.

This invention further relates to a catalyst precursor compound represented by the formula:

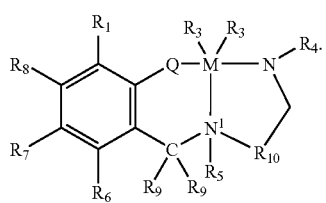

wherein:
M is a group 3 to group 12 transition metal or lanthanide metal, provided however $N^1$ is not part of a pyridine ring when M is a group 8, 9, or 10 metal;
Q is oxygen or sulfur;
N is nitrogen;
$N^1$ is nitrogen;
$R_1$, is a hydrogen, a hydrocarbyl, a substituted hydrocarbyl, a halocarbyl, a substituted halocarbyl, a heteroatom or heteratom containing group;
$R_2$ and $R_3$ are independently, a hydrogen, a halogen, a hydrocarbyl, a substituted hydrocarbyl, a halocarbyl, or a substituted halocarbyl, a heteroatom or heteratom containing group and $R_2$ and $R_3$ together may form a multidentate ligand, such as a bidentate dianionic ligand;
$R_4$ is hydrogen, a hydrocarbyl, a substituted hydrocarbyl, a halocarbyl, a substituted halocarbyl, a heteroatom or heteratom containing group;
$R_5$ is a hydrogen, a hydrocarbyl, a substituted hydrocarbyl, a halocarbyl, a substituted halocarbyl, a heteroatom or heteratom containing group;
$R_6$, $R_7$, and $R_8$ are, independently, a hydrogen, a hydrocarbyl, a substituted hydrocarbyl, a halocarbyl, a substituted halocarbyl, a heteroatom or heteratom containing group, and any two of $R_1$, $R_6$, $R_7$, and $R_8$ may form a fused ring system;
each $R_9$ is, independently, hydrogen, a hydrocarbyl, a substituted hydrocarbyl, a halocarbyl, a substituted halocarbyl group, a heteroatom or heteratom containing group;
$R_{10}$ is a hydrocarbyl, a substituted hydrocarbyl, a halocarbyl, a substituted halocarbyl group, a heteroatom or heteratom containing group;

where any two adjacent R groups may form a ring structure.

DETAILED DESCRIPTION OF THE INVENTION

This invention relates to a new class of catalyst compounds that may be combined with one or more activators to oligomerize or polymerize any unsaturated monomer.

For the purposes of this invention and the claims thereto when a polymer is referred to as comprising a monomer, the momomer present in the polymer is the polymerized form of the monomer. In the description herein the transition metal catalyst compound may be described as a catalyst precursor, a pre-catalyst compound, a transition metal complex, a transition metal compound, or a catalyst compound, and these terms are used interchangeably. A catalyst system is a combination of a transition metal catalyst compound and an activator. An activator is also interchangeably referred to as a cocatalyst.

As used herein, the numbering scheme for the Periodic Table Groups is used as in CHEMICAL AND ENGINEERING NEWS, 63(5), 27 (1985).

Further for purposes of this invention Me is methyl, Ph is phenyl, Et is ethyl, Pr is propyl, iPr is isopropyl, n-Pr is normal propyl, Bu is butyl, iBu is isobutyl, tBu is tertiary butyl, p-tBu is para-tertiary butyl, and TMS is trimethylsilyl.

The term "hydrocarbyl radical" is sometimes used interchangeably with "hydrocarbyl" throughout this document. For purposes of this disclosure, "hydrocarbyl radical" encompasses radicals containing carbon and hydrogen, preferably 1 to 100 carbon atoms. These radicals can be linear, branched, or cyclic including polycyclic. These radicals can be saturated, partially unsaturated or fully unsaturated, and when cyclic, may be aromatic or non-aromatic.

For purposes of this invention, substituted hydrocarbyl radicals (also called substituted hydrocarbyls) are radicals in which at least one hydrocarbyl hydrogen atom has been substituted with at least one heteroatom or heteroatom containing group.

In some embodiments, the hydrocarbyl radical is selected from methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, ethenyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, triacontenyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, eicosynyl, heneicosynyl, docosynyl, tricosynyl, tetracosynyl, pentacosynyl, hexacosynyl, heptacosynyl, octacosynyl, nonacosynyl, or triacontynyl isomers. For this disclosure, when a radical is listed it indicates that radical type and all other radicals formed when that radical type is subjected to the substitutions defined above. Alkyl, alkenyl and alkynyl radicals listed include all isomers including where appropriate cyclic isomers, for example, butyl includes n-butyl, 2-methylpropyl, 1-methylpropyl, tert-butyl, and cyclobutyl (and analogous substituted cyclopropyls); pentyl includes n-pentyl, cyclopentyl, 1-methylbutyl, 2-methylbutyl, 3-methylbutyl, 1-ethylpropyl, and neopentyl (and analogous substituted cyclobutyls and cyclopropyls); butenyl includes E and Z forms of 1-butenyl, 2-butenyl, 3-butenyl, 1-methyl-1-propenyl, 1-methyl-2-propenyl, 2-methyl-1-propenyl and 2-methyl-2-propenyl (and cyclobutenyls and cyclopropenyls). Cyclic compounds having branches include all isomer forms, for example, methylphenyl would include ortho-methylphenyl, meta-methylphenyl and para-methylphenyl; dimethylphenyl would include 2,3-dimethylphenyl, 2,4-dimethylphenyl, 2,5-dimethylphenyl, 2,6-dimethylphenyl, 3,4-dimethylphenyl, and 3,5-dimethylphenyl.

Functional groups are defined to be heteroatoms of groups 1–17 of the periodic table either alone or connected to other elements by covalent or other interactions such as ionic, van der Waals forces, or hydrogen bonding. Examples of functional groups include carboxylic acid, acid halide, carboxylic ester, carboxylic salt, carboxylic anhydride, aldehyde and their chalcogen (Group 16) analogues, alcohol and phenol, ether, peroxide and hydroperoxide, carboxylic amide, hydrazide and imide, amidine and other nitrogen analogues of amides, nitrile, amine and imine, azo, nitro, other nitrogen compounds, sulfur acids, selenium acids, thiols, sulfides, sulfoxides, sulfones, phosphines, phosphates, other phosphorus compounds, silanes, boranes, borates, alanes, aluminates. Functional groups may also be taken broadly to include organic polymer supports or inorganic support material such as alumina, and silica.

This invention relates to new phenoxy-amide-amine catalyst precursor compounds ("PAA") useful for olefin polymerization. In particular the catalyst precursor compound can be selected from Group 3 to 12 metals having a tridentate phenoxy-amide-amine group bound to the metal, preferably the metal is a Group 4 metal.

In preferred embodiments, the catalyst precursor compounds are represented by the formula:

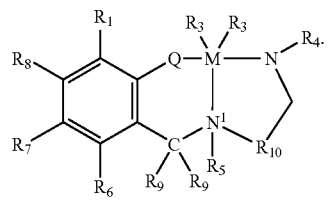

wherein:
M is a group 3 to group 12 transition metal or lanthanide metal, preferably a group 4 metal, preferably Ti, Zr or Hf, provided however $N^1$ is not part of a pyridine ring when M is a group 8, 9, or 10 metal;
Q is oxygen or sulfur, preferably oxygen;
N is nitrogen;
$N^1$ is nitrogen;
$R_1$, $R_6$, $R_7$, and $R_8$ are, independently, a hydrogen, a hydrocarbyl, a substituted hydrocarbyl, a halocarbyl, or a substituted halocarbyl; preferably at least one of $R_1$, $R_5$, $R_6$, $R_7$, and $R_8$ is not hydrogen, in another embodiment at least one of $R_1$, $R_6$, $R_7$, and $R_8$ is not hydrogen, additionally any two of $R_1$, $R_6$, $R_7$, and $R_8$ may form a fused ring system, such as a napthol.

Preferably, $R_1$, $R_6$, $R_7$ and $R_8$ are independently, hydrogen, or a $C_1$ to $C_{100}$ hydrocarbyl group, preferably an alkyl group or an aryl group, preferably a $C_1$ to $C_{20}$ alkyl group or a $C_6$ to $C_{40}$ aryl group, preferably a $C_4$ to $C_{20}$ tertiary alkyl group, preferably butyl, t-butyl, isobutyl, pentyl, hexyl, heptyl, isohexyl, octyl, isooctyl, decyl, nonyl, dodecyl, phenyl, anthracenyl, napthyl, and all isomers thereof, or a heteroatom containing group. Preferred heteroatoms include boron, aluminum, silicon, nitrogen, phosphorus, arsenic, tin, lead, antimony, oxygen, sulfur, selenium, tellurium. Particularly preferred heteroatoms include nitrogen, oxygen, phosphorus, and sulfur, preferred heteroatom groups include imines (including pyridines), amines, oxides, phosphines, ethers, carbonyls, oxazolines, thioethers, and the like.

$R_5$ is a hydrogen, a hydrocarbyl, a substituted hydrocarbyl, a halocarbyl, or a substituted halocarbyl. Preferably, $R_5$ is hydrogen, a $C_6$ to $C_{40}$ aryl group, a $C_1$ to $C_{20}$ alkyl group, a benzyl group, a substituted benzyl group, or a heteroatom containing group. Preferred heteroatoms include boron, aluminum, silicon, nitrogen, phosphorus, arsenic, tin, lead, antimony, oxygen, sulfur, selenium, tellurium. Particularly preferred heteroatoms include nitrogen, oxygen, phosphorus, and sulfur, preferred heteroatom groups include imines (including pyridines), amines, oxides, phosphines, ethers, carbonyls, oxazolines, thioethers, and the like. Preferably $R^5$ is hydrogen, methyl, ethyl, propyl, butyl, isobutyl, t-butyl, pentyl, hexyl, heptyl, octyl, nonyl, decyl, undecyl, dodecyl, phenyl, benzyl, and all isomers thereof.

$R_2$ and $R_3$ are independently, a hydrogen, a halogen, a hydrocarbyl, a substituted hydrocarbyl, a halocarbyl, or a substituted halocarbyl, a heteroatom or heteratom containing group, preferably $R_2$ and $R_3$ are each independently, an alkyl, halogen, benzyl, phenyl, amide, carboxylate, thiolate, hydride or alkoxide group, preferably a $C_1$ to $C_{100}$ alkyl group, a halogen or a phenyl group, more preferably a $C_1$ to $C_{30}$ alkyl group, preferably chlorine or bromine, particularly preferred $R_2$ and $R_3$ groups are methyl and benzyl.

In some embodiments, $R_2$ and $R_3$ are, independently, an anionic ligand, or $R_2$ and $R_3$ together may form a multidentate ligand, such as a bidentate dianionic ligand.

$R_4$ is hydrogen, a hydrocarbyl, a substituted hydrocarbyl, a halocarbyl, or a substituted halocarbyl. Preferably $R_4$ is hydrogen, or a $C_1$ to $C_{100}$ hydrocarbyl, preferably a $C_1$ to $C_{20}$ alkyl group, a $C_6$ to $C_{40}$ aromatic group, preferably a phenyl group or substituted phenyl group, more preferably a phenyl substituted at the 2 and/or 6 positions, more preferably a phenyl substituted at the 2, 4, and 6 positions, preferably a phenyl substituted at the 2, 4, and 6 positions with $C_1$ to $C_{40}$ hydrocarbyls, examples of which include, but are not limited to, methyl, ethyl, propyl, isopropyl, butyl, isobutyl, t-butyl, neopentyl, phenyl, phenyls substituted with $C_1$ to $C_{40}$ hydrocarbyls, and the like. $R_4$ may also be a heteroatom or heteratom containing group. Preferred heteroatoms include nitrogen, oxygen, phosphorus and sulfur. Preferred heteroatom containing groups include phosphines, imines (including pyridines), amines, oxides, ethers, carbonyls, oxazolines, thioethers, and the like. In a preferred embodiment $R_4$ is a halogenated phenyl group, preferably a phenyl group substituted at the 2 or 6 positions with a halogen atom, more preferably a phenyl group substituted at the 2 and 6 positions with a halogen atom. The halogen atom is preferably Br or Cl.

Each $R_9$ is, independently, hydrogen, a hydrocarbyl, a substituted hydrocarbyl, a halocarbyl, or a substituted halocarbyl group, preferably having 1 to 10 carbon atoms, preferably 1 to 6 carbon atoms, more preferably 1, 2 or 3 carbon atoms. In a particularly preferred embodiment both $R_9$ groups are hydrogen.

$R_{10}$ is a hydrocarbyl, a substituted hydrocarbyl, a halocarbyl, or a substituted halocarbyl group, preferably having 1 to 10 carbon atoms, preferably 1 to 6 carbon atoms, more preferably 1, 2 or 3 carbon atoms, provided that when $R_{10}$ contains two or more carbon atoms, it may be contained within a cyclic group, which may be fused, saturated, unsaturated, or polycyclic.

Any two adjacent R groups may form a ring structure, preferably a 5 or 6 membered ring. Likewise the R groups may form multi-ring structures.

Preferred catalyst precursor compounds include those represented by the following formulae:

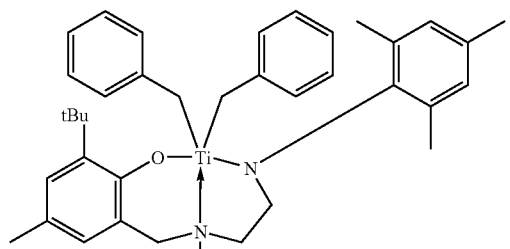

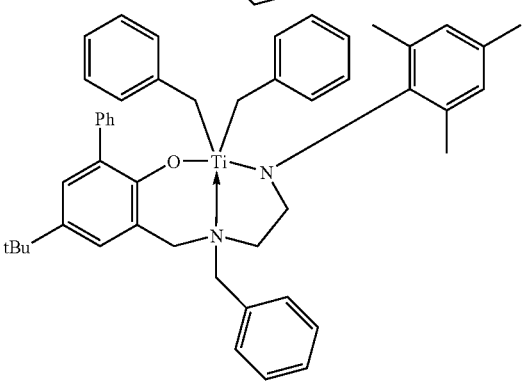

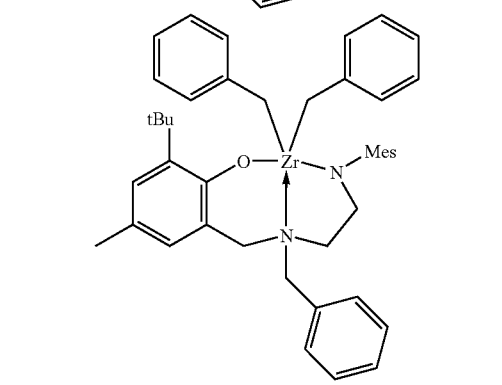

-continued

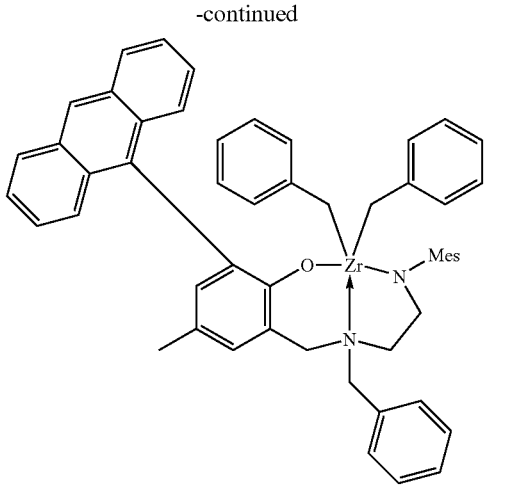

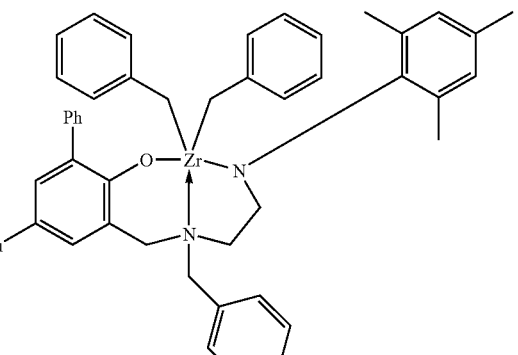

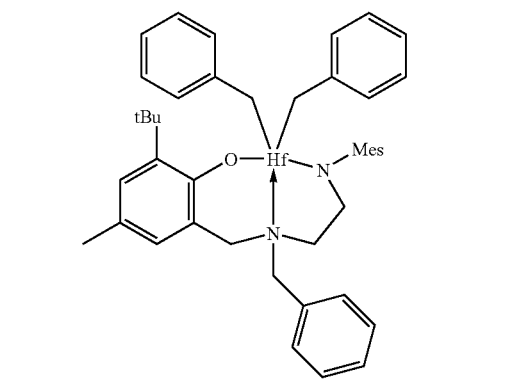

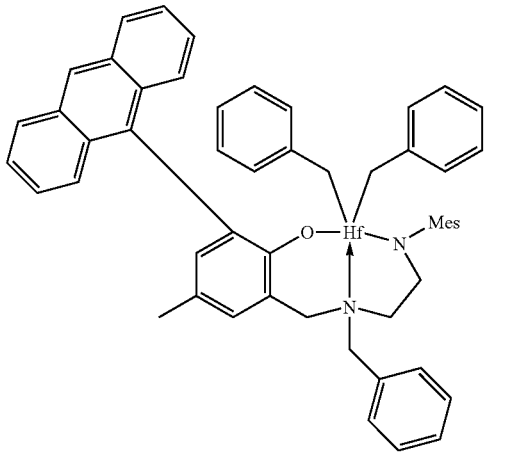

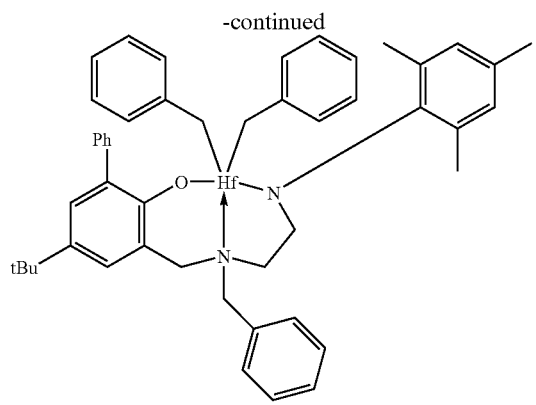
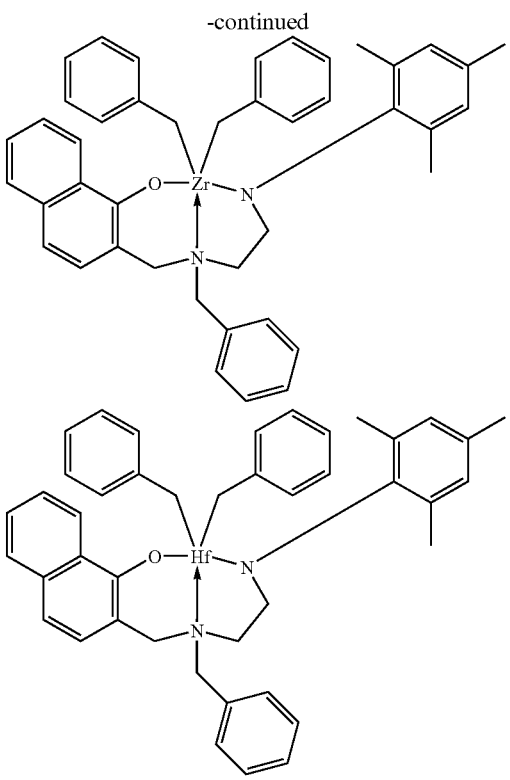
where Mes is mesityl, tBu is tertiary butyl, Ph is phenyl.
A typical synthesis procedure to make the catalyst precursor compounds is shown below:
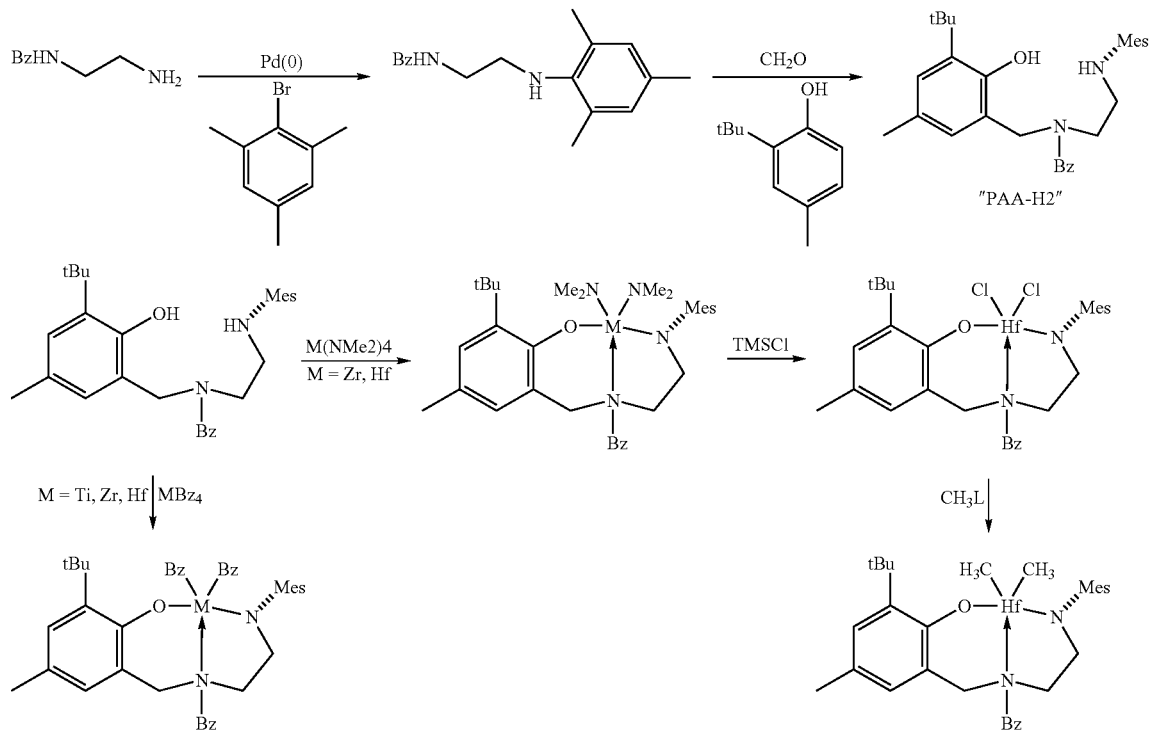

where tBu is tertiary butyl, Bz is benzyl, Mes is mesityl, Me is methyl, M is Hf or Zr, TMSCl is Me$_3$SiCl, and CH$_3$I is methyliodide.

Activators and Activation Methods for Catalyst Compounds

An activator is defined as any combination of reagents that increases the rate at which a transition metal compound oligomerizes or polymerizes unsaturated monomers, such as olefins. An activator may also affect the molecular weight, degree of branching, comonomer content, or other properties of the oligomer or polymer. The transition metal compounds according to the invention may be activated for oligomerization and or polymerization catalysis in any manner sufficient to allow coordination or cationic oligomerization and or polymerization.

Generally speaking, successful olefin oligomerization and/or polymerization catalysts contain a formal anionic ligand, such as hydride or hydrocarbyl, with an adjacent (cis) coordination site accessible to an unsaturated monomer. Coordination of an unsaturated monomer to the cis coordination site allows a migratory insertion reaction to form a metal alkyl. Repetition of this process causes chain growth. An activator is thus any combination of reagents that facilitates formation of a transition metal compound containing cis coordinated olefin and hydride or hydrocarbyl.

When the transition metal compound contains at least one hydride or hydrocarbyl ligand, activation can be achieved by removal of formal anionic or neutral ligands, of higher binding affinity than the unsaturated monomer. This removal, also called abstraction, process may have a kinetic rate that is first-order or non-first order with respect to the activator. Activators that remove anonic ligands are termed ionizing activators. Activators that remove neutral ligands are termed non-ionizing activators. Activators are typically strong Lewis-acids which may play either the role of ionizing or non-ionizing activator.

When the transition metal compound does not contain at least one hydride or hydrocarbyl ligands, then activation may be a one step or multi step process. One step in this process includes coordinating a hydride or hydrocarbyl group to the metal compound. A separate activation step is removal of anionic or neutral ligands of higher binding affinity than the unsaturated monomer. These activation steps may occur in series or in parallel. These steps may occur in the presence of olefin. These steps may occur prior to exposure to olefin. More than one sequence of activation steps is possible to achieve activation.

The activator may also act to coordinate a hydride or hydrocarbyl group to the transition metal compound. When the transition metal compound does not contain at least one hydride or hydrocarbyl ligands but does contain at least one functional group ligand, activation may be effected by substitution of the functional group with a hydride, hydrocarbyl or substituted hydrocarbyl group. This substitution may be effected with appropriate hydride or alkyl reagents of group 1, 2, 12, 13 elements as is known in the art. To achieve activation, it may be necessary to also remove anionic or neutral ligands of higher binding affinity than the unsaturated monomer.

Alumoxane and aluminum alkyl activators are capable of alkylation and abstraction activation.

The activator may also act to coordinate a hydride or hydrocarbyl group to the transition metal compound. If the transition metal compound does not contain anionic ligands, then a hydride, hydrocarbyl or substituted hydrocarbyl may be coordinated to a metal using electrophilic proton or alkyl transfer reagents represented by H$^+$(LB)$_n$A$^-$, (R$^9$)$^+$(LB)$_n$A$^-$. R$^9$ is a hydrocarbyl or a substituted hydrocarbyl; LB is a Lewis-base, n=0, 1 or 2. Non-limiting examples of preferred Lewis-bases are diethyl ether, dimethyl ether, ethanol, methanol, water, acetonitrile, N,N-dimethylaniline. A$^-$ is an anion preferably a substituted hydrocarbon, a functional group, or a non-coordinating anion. Non-limiting examples of A$^-$ include halides, carboxylates, phosphates, sulfates, sulfonates, borates, aluminates, alkoxides, thioalkoxides, anionic substituted hydrocarbons, and anionic metal complexes.

A. Aluminoxane and Aluminum Alkyl Activators

In one embodiment, alumoxanes activators are utilized as an activator in the catalyst composition of the invention. Alumoxanes are generally oligomeric compounds containing —Al(R)—O— subunits, where R is an alkyl group. Examples of alumoxanes include methylalumoxane (MAO), modified methylalumoxane (MMAO), ethylalumoxane and isobutylalumoxane. Alkylalumoxanes and modified alkylalumoxanes are suitable as catalyst activators, particularly when the abstractable ligand is a halide. Mixtures of different alumoxanes and modified alumoxanes may also be used. For further descriptions, see U.S. Pat. Nos. 4,665,208, 4,952,540, 5,041,584, 5,091,352, 5,206,199, 5,204,419, 4,874,734, 4,924,018, 4,908,463, 4,968,827, 5,329,032, 5,248,801, 5,235,081, 5,157,137, 5,103,031 and EP 0 561 476 A1, EP 0 279 586 B1, EP 0 516 476 A, EP 0 594 218 A1 and WO 94/10180.

When the activator is an alumoxane (modified or unmodified), some embodiments select the maximum amount of activator at a 5000-fold molar excess Al/M over the catalyst precursor (per metal catalytic site). The minimum activator-to-catalyst-precursor is a 1:1 molar ratio.

Alumoxanes may be produced by the hydrolysis of the respective trialkylaluminum compound. MMAO may be produced by the hydrolysis of trimethylaluminum and a higher trialkylaluminum such as triisobutylaluminum. MMAO's are generally more soluble in aliphatic solvents and more stable during storage. There are a variety of methods for preparing alumoxane and modified alumoxanes, non-limiting examples of which are described in U.S. Pat. Nos. 4,665,208, 4,952,540, 5,091,352, 5,206,199, 5,204,419, 4,874,734, 4,924,018, 4,908,463, 4,968,827, 5,308,815, 5,329,032, 5,248,801, 5,235,081, 5,157,137, 5,103,031, 5,391,793, 5,391,529, 5,693,838, 5,731,253, 5,731,451, 5,744,656, 5,847,177, 5,854,166, 5,856,256 and 5,939,346 and European publications EP-A-0 561 476, EP-B1-0 279 586, EP-A-0 594-218 and EP-B1-0 586 665, and PCT publications WO 94/10180 and WO 99/15534, all of which are herein fully incorporated by reference. It may be preferable to use a visually clear methylalumoxane. A cloudy or gelled alumoxane can be filtered to produce a clear solution or clear alumoxane can be decanted from the cloudy solution. Another alumoxane is a modified methyl alumoxane (MMAO) cocatalyst type 3A (commercially available from Akzo Chemicals, Inc. under the trade name Modified Methylalumoxane type 3A, covered under U.S. Pat. No. 5,041,584).

Aluminum alkyl or organoaluminum compounds which may be utilized as activators (or scavengers) include trimethylaluminum, triethylaluminum, triisobutylaluminum, tri-n-hexylaluminum, tri-n-octylaluminum and the like.

B. Ionizing Activators

It is within the scope of this invention to use an ionizing or stoichiometric activator, neutral or ionic, such as tri (n-butyl) ammonium tetrakis (pentafluorophenyl) boron, a trisperfluorophenyl boron metalloid precursor or a trisperfluoronaphtyl boron metalloid precursor, polyhalogenated heteroborane anions (WO 98/43983), boric acid (U.S. Pat. No. 5,942,459) or combination thereof. It is also within the scope of this invention to use neutral or ionic activators alone or in combination with alumoxane or modified alumoxane activators.

Examples of neutral stoichiometric activators include tri-substituted boron, tellurium, aluminum, gallium and indium or mixtures thereof. The three substituent groups are each independently selected from alkyls, alkenyls, halogen, substituted alkyls, aryls, arylhalides, alkoxy and halides. Preferably, the three groups are independently selected from halogen, mono or multicyclic (including halosubstituted) aryls, alkyls, and alkenyl compounds and mixtures thereof, preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). More preferably, the three groups are alkyls having 1 to 4 carbon groups, phenyl, napthyl or mixtures thereof. Even more preferably, the three groups are halogenated, preferably fluorinated, aryl groups. Most preferably, the neutral stoichiometric activator is trisperfluorophenyl boron or trisperfluoronapthyl boron.

Ionic stoichiometric activator compounds may contain an active proton, or some other cation associated with, but not coordinated to, or only loosely coordinated to, the remaining ion of the ionizing compound. Such compounds and the like are described in European publications EP-A-0 570 982, EP-A-0 520 732, EP-A-0 495 375, EP-B1-0 500 944, EP-A-0 277 003 and EP-A-0 277 004, and U.S. Pat. Nos. 5,153,157, 5,198,401, 5,066,741, 5,206,197, 5,241,025, 5,384,299 and 5,502,124 and U.S. patent application Ser. No. 08/285,380, filed Aug. 3, 1994, all of which are herein fully incorporated by reference.

Preferred activators include a cation and an anion component, and may be represented by the following formula:

$$(W^{f+})_g(NCA^{h-})_i$$

$W^{f+}$ is a cation component having the charge f+
$NCA^{h-}$ is a non-coordinating anion having the charge h−
f is an integer from 1 to 3.
h is an integer from 1 to 3.
g and h are constrained by the relationship: (g)×(f)=(h)×(i).

The cation component, ($W^{f+}$) may include Bronsted acids such as protons or protonated Lewis bases or reducible Lewis acids capable of protonating or abstracting a moiety, such as an akyl or aryl, from an analogous metallocene or Group 15 containing transition metal catalyst precursor, resulting in a cationic transition metal species.

In a preferred embodiment, the activators include a cation and an anion component, and may be represented by the following formula:

$$(LB-H^{f+})_g(NCA^{h-})_i$$

wherein LB is a neutral Lewis base;
H is hydrogen;
$NCA^{h-}$ is a non-coordinating anion having the charge h−
f is an integer from 1 to 3,
h is an integer from 1 to 3,
g and h are constrained by the relationship: (g)×(f)−(h)×(i).

The activating cation ($W^{f+}$) may be a Bronsted acid, (LB-$H^{f+}$), capable of donating a proton to the transition metal catalytic precursor resulting in a transition metal cation, including ammoniums, oxoniums, phosphoniums, silyliums and mixtures thereof, preferably ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxoniums from ethers such as dimethyl ether diethyl ether, tetrahydrofuran and dioxane, sulfoniums from thioethers, such as diethyl thioethers and tetrahydrothiophene and mixtures thereof.

The activating cation ($W^{f+}$) may also be an abstracting moiety such as silver, carboniums, tropylium, carbeniums, ferroceniums and mixtures, preferably carboniums and ferroceniums. Most preferably ($W^{f+}$) is triphenyl carbonium or N, N-dimethylanilinium.

The anion component ($NCA^{h-}$) includes those having the formula $[T^{j+}Q_k]^{h-}$ wherein j is an integer from 1 to 3; k is an integer from 2 to 6; k−j=h; T is an element selected from Group 13 or 15 of the Periodic Table of the Elements, preferably boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than 1 occurrence is Q a halide. Preferably, each Q is a fluorinated hydrocarbyl group having 1 to 20 carbon atoms, more preferably each Q is a fluorinated aryl group, and most preferably each Q is a pentafluoryl aryl group. Examples of suitable ($NCA^{h-}$) also include diboron compounds as disclosed in U.S. Pat. No. 5,447,895, which is fully incorporated herein by reference.

Additional suitable anions are known in the art and will be suitable for use with the catalysts of the invention. See in particular, U.S. Pat. No. 5,278,119 and the review articles by S. H. Strauss, "The Search for Larger and More Weakly Coordinating Anions", Chem. Rev., 93, 927–942 (1993) and C. A. Reed, "Carboranes: A New Class of Weakly Coordinating Anions for Strong Electrophiles, Oxidants and Superacids", Acc. Chem. Res., 31, 133–139 (1998).

Illustrative, but not limiting examples of boron compounds which may be used as an activating cocatalyst in the preparation of the improved catalysts of this invention are tri-substituted ammonium salts such as:
trimethylammonium tetraphenylborate,
triethylammonium tetraphenylborate,
tripropylammonium tetraphenylborate,
tri(n-butyl)ammonium tetraphenylborate,
tri(t-butyl)ammonium tetraphenylborate,
N,N-dimethylanilinium tetraphenylborate,
N,N-diethylanilinium tetraphenylborate,
N,N-dimethyl-(2,4,6-trimethylanilinium) tetraphenylborate,
trimethylammonium tetrakis(pentafluorophenyl)borate,
triethylammonium tetrakis(pentafluorophenyl)borate,
tripropylammonium tetrakis(pentafluorophenyl)borate,
tri(n-butyl)ammonium tetrakis(pentafluorophenyl)borate,
tri(sec-butyl)ammonium tetrakis(pentafluorophenyl) borate,
N,N-dimethylanilinium tetrakis(pentafluorophenyl) borate,
N,N-diethylanilinium tetrakis(pentafluorophenyl) borate,
N,N-dimethyl-(2,4,6-trimethylanilinium) tetrakis(pentafluorophenyl) borate,
trimethylammonium tetrakis-(2,3,4,6-tetrafluorophenylborate,
triethylammonium tetrakis-(2,3,4,6-tetrafluorophenyl) borate,
tripropylammonium tetrakis-(2,3,4,6-tetrafluorophenyl) borate, tri(n-butyl)ammonium tetrakis-(2,3,4,6-tetrafluoro-phenyl) borate,
dimethyl(t-butyl)ammonium tetrakis-(2,3,4,6-tetrafluorophenyl) borate,
N,N-dimethylanilinium tetrakis-(2,3,4,6-tetrafluorophenyl) borate,
N,N-diethylanilinium tetrakis-(2,3,4,6-tetrafluoro-phenyl) borate, and
N,N-dimethyl-(2,4,6-trimethylanilinium)tetrakis-(2,3,4,6-tetrafluorophenyl) borate;
dialkyl ammonium salts such as: di-(i-propyl)ammonium tetrakis(pentafluorophenyl) borate, and dicyclohexylammonium tetrakis(pentafluorophenyl) borate; and tri-substituted phosphonium salts such as: triphenylphosphonium tetrakis(pentafluorophenyl) borate, tri(o-tolyl) phosphonium tetrakis(pentafluorophenyl) borate, and tri (2,6-dimethylphenyl)phosphonium tetrakis (pentafluorophenyl) borate.

Most preferably, the ionic stoichiometric activator is N,N-dimethylanilinium tetra(perfluorophenyl)borate or triphenylcarbenium tetra(perfluorophenyl)borate.

In one embodiment, an activation method using ionizing ionic compounds not containing an active proton but capable of producing a bulky ligand metallocene catalyst cation and their non-coordinating anion are also contemplated, and are described in EP-A-0 426 637, EP-A-0 573 403 and U.S. Pat. No. 5,387,568, which are all herein incorporated by reference.

The term "non-coordinating anion" (NCA) means an anion which either does not coordinate to said cation or which is only weakly coordinated to said cation thereby remaining sufficiently labile to be displaced by a neutral Lewis base. "Compatible" non-coordinating anions are those which are not degraded to neutrality when the initially formed complex decomposes. Non-coordinating anions useful in accordance with this invention are those that are compatible, stabilize the metal cation in the sense of balancing its ionic charge, yet retain sufficient lability to permit displacement by an ethylenically or acetylenically unsaturated monomer during polymerization. These types of cocatalysts sometimes use tri-isobutyl aluminum or tri-octyl aluminum as a scavenger.

Invention process also can employ cocatalyst compounds or activator compounds that are initially neutral Lewis acids but form a cationic metal complex and a noncoordinating anion, or a zwitterionic complex upon reaction with the invention compounds. For example, tris(pentafluorophenyl) boron or aluminum act to abstract a hydrocarbyl or hydride ligand to yield an invention cationic metal complex and stabilizing noncoordinating anion, see EP-A-0 427 697 and EP-A-0 520 732 for illustrations of analogous Group-4 metallocene compounds. Also, see the methods and compounds of EP-A-0 495 375. For formation of zwitterionic complexes using analogous Group 4 compounds, see U.S. Pat. Nos. 5,624,878; 5,486,632; and 5,527,929.

Additional neutral Lewis-acids are known in the art and are suitable for abstracting anionic ligands. See in particular the review article by E. Y.-X. Chen and T. J. Marks, "Cocatalysts for Metal-Catalyzed Olefin Polymerization: Activators, Activation Processes, and Structure-Activity Relationships", Chem. Rev., 100, 1391–1434 (2000).

When the transition metal compound does not contain at least one hydride or hydrocarbyl ligand but does contain at least one functional group ligand, such as chloride, amido or alkoxy ligands, and the functional group ligands are not capable of discrete ionizing abstraction with the ionizing, anion pre-cursor compounds, these functional group ligands can be converted via known alkylation reactions with organometallic compounds such as lithium or aluminum hydrides or alkyls, alkylalumoxanes, Grignard reagents, etc. See EP-A-0 500 944, EP-A1-0 570 982 and EP-A1-0 612 768 for analogous processes describing the reaction of alkyl aluminum compounds with analogous dihalide substituted metallocene compounds prior to or with the addition of activating noncoordinating anion precursor compounds.

C. Non-ionizing Activators

Activators are typically strong Lewis-acids which may play either the role of ionizing or non-ionizing activator. Activators previously described as ionizing activators may also be used as non-ionizing activators.

Abstraction of formal neutral ligands may be achieved with Lewis acids that display an affinity for the formal neutral ligands. These Lewis acids are typically unsaturated or weakly coordinated. Examples of non-ionizing activators include $R^{10}(R^{11})_3$, where $R^{10}$ is a group 13 element and $R^{11}$ is a hydrogen, a hydrocarbyl, a substituted hydrocarbyl, or a functional group. Typically, $R^{11}$ is an arene or a perfluorinated arene. Non-ionizing activators also include weakly coordinated transition metal compounds such as low valent olefin complexes. Non-limiting examples of non-ionizing activators include $BMe_3$, $BEt_3$, $B(iBu)_3$, $BPh_3$, $B(C_6F_5)_3$, $AlMe_3$, $AlEt_3$, $Al(iBu)_3$, $AlPh_3$, $B(C_6F_5)_3$, alumoxane, CuCl, $Ni(1,5\text{-cyclooctadiene})_2$.

Additional neutral Lewis-acids are known in the art and will be suitable for abstracting neutral ligands. See in particular the review article by E. Y.-X. Chen and T. J. Marks, "Cocatalysts for Metal-Catalyzed Olefin Polymerization: Activators, Activation Processes, and Structure-Activity Relationships", Chem. Rev., 100, 1391–1434 (2000).

Preferred non-ionizing activators include $R^{10}(R^{11})_3$, where $R^{10}$ is a group 13 element and $R^{11}$ is a hydrogen, a hydrocarbyl, a substituted hydrocarbyl, or a functional group. Typically, $R^{11}$ is an arene or a perfluorinated arene.

More preferred non-ionizing activators include $B(R^{12})_3$, where $R^{12}$ is an arene or a perfluorinated arene. Even more preferred non-ionizing activators include $B(C_6H_5)_3$ and $B(C_6F_5)_3$. A particularly preferred non-ionizing activator is $B(C_6F_5)_3$. More preferred activators are ionizing and non-ionizing activators based on perfluoroaryl borane and perfluoroaryl borates such as $PhNMe_2H^+$ $B(C_6F_5)_4^-$, $(C_6H_5)_3C^+$ $B(C_6F_5)_4^-$, and $B(C_6F_5)_3$.

When the cations of noncoordinating anion precursors are Bronsted acids such as protons or protonated Lewis bases (excluding water), or reducible Lewis acids such as ferrocenium or silver cations, or alkali or alkaline earth metal cations such as those of sodium, magnesium or lithium, the catalyst-precursor-to-activator molar ratio may be any ratio. Combinations of the described activator compounds may also be used for activation. For example, tris(perfluorophenyl) boron can be used with methylalumoxane.

In general the precursor compounds and the activator are combined in ratios of about 1000:1 to about 0.5:1. In a preferred embodiment the precursor compounds and the activator are combined in a ratio of about 300:1 to about 1:1, preferably about 150:1 to about 1:1, for boranes, borates, aluminates, etc. the ratio is preferably about 1:1 to about 10:1 and for alkyl aluminum compounds (such as diethylaluminum chloride combined with water) the ratio is preferably about 0.5:1 to about 10:1.

In a preferred embodiment two or more catalyst precursor compounds may be present. In some embodiments the ratio of the first catalyst precursor compound to the second or additional catalyst precursor compounds is 5:95 to 95:5, preferably 25:75 to 75:25, even more preferably 40:60 to 60:40.

In another embodiment the catalyst compositions of this invention include a support material or carrier. For example, the one or more catalyst components and/or one or more activators may be deposited on, contacted with, vaporized with, bonded to, or incorporated within, adsorbed or absorbed in, or on, one or more supports or carriers.

The support material is any of the conventional support materials. Preferably the supported material is a porous support material, for example, talc, inorganic oxides and inorganic chlorides. Other support materials include resinous support materials such as polystyrene, functionalized or crosslinked organic supports, such as polystyrene divinyl benzene polyolefins or polymeric compounds, zeolites, clays, or any other organic or inorganic support material and the like, or mixtures thereof.

The preferred support materials are inorganic oxides that include those Group 2, 3, 4, 5, 13 or 14 metal oxides. The preferred supports include silica, which may or may not be dehydrated, fumed silica, alumina (WO 99/60033), silica-alumina and mixtures thereof. Other useful supports include magnesia, titania, zirconia, magnesium chloride (U.S. Pat. No. 5,965,477), montmorillonite (European Patent EP-B1 0 511 665), phyllosilicate, zeolites, talc, clays (U.S. Pat. No. 6,034,187) and the like. Also, combinations of these support materials may be used, for example, silica-chromium, silica-alumina, silica-titania and the like. Additional support materials may include those porous acrylic polymers described in EP 0 767 184 B1, which is incorporated herein by reference. Other support materials include nanocomposites as described in PCT WO 99/47598, aerogels as described in WO 99/48605, spherulites as described in U.S. Pat. No. 5,972,510 and polymeric beads as described in WO 99/50311, which are all herein incorporated by reference.

It is preferred that the support material, most preferably an inorganic oxide, has a surface area in the range of from about 10 to about 700 m$^2$/g, pore volume in the range of from about 0.1 to about 4.0 cc/g and average particle size in the range of from about 5 to about 500 µm. More preferably, the surface area of the support material is in the range of from about 50 to about 500 m$^2$/g, pore volume of from about 0.5 to about 3.5 cc/g and average particle size of from about 10 to about 200 µm. Most preferably the surface area of the support material is in the range is from about 100 to about 400 m$^2$/g, pore volume from about 0.8 to about 3.0 cc/g and average particle size is from about 5 to about 100 µm. The average pore size of the carrier of the invention typically has pore size in the range of from 10 to 1000 Å, preferably 50 to about 500 Å, and most preferably 75 to about 350 Å.

Monomers

In a preferred embodiment the transition metal compounds of this invention are used to polymerize or oligomerize any unsaturated monomer or monomers. Preferred monomers include $C_2$ to $C_{100}$ olefins, preferably $C_2$ to $C_{60}$ olefins, preferably $C_2$ to $C_{40}$ olefins preferably $C_2$ to $C_{20}$ olefins, preferably $C_2$ to $C_{12}$ olefins. In some embodiments preferred monomers include linear, branched or cyclic alpha-olefins, preferably $C_2$ to $C_{100}$ alpha-olefins, preferably $C_2$ to $C_{60}$ alpha-olefins, preferably $C_2$ to $C_{40}$ alpha-olefins preferably $C_2$ to $C_{20}$ alpha-olefins, preferably $C_2$ to $C_{12}$ alpha-olefins. Preferred olefin monomers may be one or more of ethylene, propylene, butene, pentene, hexene, heptene, octene, nonene, decene, dodecene, 4-methyl-pentene-1,3-methyl pentene-1,3,5,5-trimethyl hexene 1, and 5-ethyl-1-nonene.

In another embodiment the polymer produced herein is a copolymer of one or more linear or branched $C_3$ to $C_{30}$ prochiral alpha-olefins or $C_5$ to $C_{30}$ ring containing olefins or combinations thereof capable of being polymerized by either stereospecific and non-stereospecific catalysts. Prochiral, as used herein, refers to monomers that favor the formation of isotactic or syndiotactic polymer when polymerized using stereospecific catalyst(s).

Other monomers may also include aromatic-group-containing monomers containing up to 30 carbon atoms. Suitable aromatic-group-containing monomers comprise at least one aromatic structure, preferably from one to three, more preferably a phenyl, indenyl, fluorenyl, or naphthyl moiety. The aromatic-group-containing monomer further comprises at least one polymerizable double bond such that after polymerization, the aromatic structure will be pendant from the polymer backbone. The aromatic-group containing monomer may further be substituted with one or more hydrocarbyl groups including but not limited to $C_1$ to $C_{10}$ alkyl groups. Additionally two adjacent substitutions may be joined to form a ring structure. Preferred aromatic-group-containing monomers contain at least one aromatic structure appended to a polymerizable olefinic moiety. Particularly preferred aromatic monomers include styrene, alpha-methylstyrene, para-alkylstyrenes, vinyltoluenes, vinylnaphthalene, allyl benzene, and indene, especially styrene, para-methylstyrene, 4-phenyl-1-butene and allyl benzene.

Non aromatic cyclic group containing monomers are also preferred. These monomers can contain up to 30 carbon atoms. Suitable non-aromatic cyclic group containing monomers preferably have at least one polymerizable olefinic group that is either pendant on the cyclic structure or is part of the cyclic structure. The cyclic structure may also be further substituted by one or more hydrocarbyl groups such as, but not limited to, $C_1$ to $C_{10}$ alkyl groups. Preferred non-aromatic cyclic group containing monomers include vinylcyclohexane, vinylcyclohexene, vinylnorbornene, ethylidene norbornene, cyclopentadiene, cyclopentene, cyclohexene, cyclobutene, vinyladamantane and the like.

Preferred diolefin monomers useful in this invention include any hydrocarbon structure, preferably $C_4$ to $C_{30}$, having at least two unsaturated bonds, wherein at least one, typically two, of the unsaturated bonds are readily incorporated into a polymer by either a stereospecific or a non-stereospecific catalyst(s). It is further preferred that the diolefin monomers be selected from alpha, omega-diene monomers (i.e. di-vinyl monomers). More preferably, the diolefin monomers are linear di-vinyl monomers, most preferably those containing from 4 to 30 carbon atoms. Examples of preferred dienes include butadiene, pentadiene, hexadiene, heptadiene, octadiene, nonadiene, decadiene, undecadiene, dodecadiene, tridecadiene, tetradecadiene, pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, particularly preferred dienes include 1,6-heptadiene, 1,7-octadiene, 1,8-nonadiene, 1,9-decadiene, 1,10-undecadiene, 1,11-dodecadiene, 1,12-tridecadiene, 1,13-tetradecadiene, and low molecular weight polybutadienes (Mw less than 1000 g/mol). Preferred cyclic dienes include cyclopentadiene, vinylnorbornene, norbornadiene, ethylidene norbornene, divinylbenzene, dicyclopentadiene or higher ring containing diolefins with or without substituents at various ring positions.

For purposes of this disclosure, the term oligomer refers to compositions having 2–75 mer units and the term polymer refers to compositions having 76 or more mer units. A mer is defined as a unit of an oligomer or polymer that originally corresponded to the olefin(s) used in the oligomerization or polymerization reaction. For example, the mer of polyethylene would be ethylene.

In an embodiment herein, the process described herein is used to produce an oligomer of any of the monomers listed above. Preferred oligomers include oligomers of any $C_2$ to $C_{20}$ olefins, preferably $C_2$ to $C_{12}$ alpha-olefins, most preferably oligomers comprising ethylene, propylene and or butene are prepared. A preferred feedstock for the oligomerization process is the alpha-olefin, ethylene. But other alpha-olefins, including but not limited to propylene and 1-butene, may also be used alone or combined with ethylene. Preferred alpha-olefins include any $C_2$ to $C_{40}$ alpha-olefin, preferably and $C_2$ to $C_{20}$ alpha-olefin, preferably any $C_2$ to $C_{12}$ alpha-olefin, preferably ethylene, propylene, and butene, most preferably ethylene. Dienes may be used in the processes described herein, preferably alpha, omega-dienes are used alone or in combination with mono-alpha olefins.

In a preferred embodiment the process described herein may be used to produce homopolymers or copolymers. (For the purposes of this invention and the claims thereto a copolymer may comprise two, three, four or more different monomer units.) Preferred polymers produced herein include homopolymers or copolymers of any of the above monomers. In a preferred embodiment the polymer is a homopolymer of any $C_2$ to $C_{12}$ alpha-olefin. Preferably the polymer is a homopolymer of ethylene or a homopolymer of propylene. In another embodiment the polymer is a copolymer comprising ethylene and one or more of any of the monomers listed above. In another embodiment the polymer is a copolymer comprising propylene and one or more of any of the monomers listed above. In another preferred embodiment the copolymers comprises one or more diolefin comonomers, preferably one or more $C_2$ to $C_{40}$ diolefins.

In another preferred embodiment the polymer produced herein is a copolymer of ethylene and one or more $C_3$ to $C_{20}$ linear, branched or cyclic monomers, preferably one or more $C_3$ to $C_{12}$ linear, branched or cyclic alpha-olefins. Preferably the polymer produced herein is a copolymer of ethylene and one or more of propylene, butene, pentene, hexene, heptene, octene, nonene, decene, dodecene, 4-methyl-pentene-1,3-methyl pentene-1, and 3,5,5-trimethyl hexene 1.

In another preferred embodiment the polymer produced herein is a copolymer of propylene and one or more $C_2$ or $C_4$ to $C_{20}$ linear, branched or cyclic monomers, preferably one or more $C_2$ or $C_4$ to $C_{12}$ linear, branched or cyclic alpha-olefins. Preferably the polymer produced herein is a copolymer of propylene and one or more of ethylene, butene, pentene, hexene, heptene, octene, nonene, decene, dodecene, 4-methyl-pentene-1, 3-methyl pentene-1, and 3,5,5-trimethyl hexene 1.

In a preferred embodiment the copolymers described herein comprise at least 50 mole % of a first monomer and up to 50 mole % of other monomers.

In a preferred embodiment the polymers described above further comprise one or more dienes at up to 10 weight %, preferably at 0.00001 to 1.0 weight %, preferably 0.002 to 0.5 weight %, even more preferably 0.003 to 0.2 weight %, based upon the total weight of the composition. In some embodiments 500 ppm or less of diene is added to the polymerization, preferably 400 ppm or less, preferably or 300 ppm or less. In other embodiments at least 50 ppm of diene is added to the polymerization, or 100 ppm or more, or 150 ppm or more.

Polymerization Processes

Typically one or more transition metal compounds, one or more activators, and one or more monomers are contacted to produce polymer. The components may be contacted in a solution, bulk, gas or slurry polymerization process or a combination thereof, preferably solution phase or bulk phase polymerization process.

In general the transition metal compound and the activator are combined in ratios of about 1:10,000 to about 1:1, in other embodiments the combined transition metal compounds and the activator are combined in ratios of 1:1 to 100:1. When alumoxane or aluminum alkyl activators are used, the combined pre-catalyst-to-activator molar ratio is from 1:5000 to 10:1, alternatively from 1:1000 to 10:1; alternatively, 1:500 to 2:1; or 1:300 to 1:1. When ionizing activators are used, the combined pre-catalyst-to-activator molar ratio is from 10:1 to 1:10; 5:1 to 1:5; 2:1 to 1:2; or 1.2:1 to 1:1. Multiple activators may be used, including using mixtures of alumoxanes or aluminum alkyls with ionizing activators.

One or more reactors in series or in parallel may be used in the present invention. Catalyst component and activator may be delivered as a solution or slurry, either separately to the reactor, activated in-line just prior to the reactor, or preactivated and pumped as an activated solution or slurry to the reactor. A preferred operation is two solutions activated in-line. Polymerizations are carried out in either single reactor operation, in which monomer, comonomers, catalyst/activator, scavenger, and optional modifiers are added continuously to a single reactor or in series reactor operation, in which the above components are added to each of two or more reactors connected in series. The catalyst components can be added to the first reactor in the series. The catalyst component may also be added to both reactors, with one component being added to first reaction and another component to other reactors.

Ethylene-alpha-olefin (including ethylene-cyclic olefin and ethylene-alpha-olefin-diolefin) elastomers of high molecular weight and low crystallinity can be prepared utilizing the catalysts of the invention under traditional solution processes or by introducing ethylene gas into a slurry utilizing the alpha-olefin or cyclic olefin or mixture thereof with other monomers, polymerizable and not, as a polymerization diluent in which the catalyst suspension is suspended. Typical ethylene pressures will be between 10 and 1000 psig (69–6895 kPa) and the polymerization diluent temperature will typically be between −10 and 160° C. The process can be carried out in a stirred tank reactor or a tubular reactor, or more than one reactor operated in series or in parallel. See the general disclosure of U.S. Pat. No. 5,001,205 for general process conditions. All documents are incorporated by reference for description of polymerization processes, ionic activators and useful scavenging compounds.

Gas Phase Polymerization

Generally, in a fluidized gas bed process used for producing polymers, a gaseous stream containing one or more monomers is continuously cycled through a fluidized bed in the presence of a catalyst under reactive conditions. The gaseous stream is withdrawn from the fluidized bed and recycled back into the reactor. Simultaneously, polymer product is withdrawn from the reactor and fresh monomer is added to replace the polymerized monomer. (See for example U.S. Pat. Nos. 4,543,399, 4,588,790, 5,028,670, 5,317,036, 5,352,749, 5,405,922, 5,436,304, 5,453,471, 5,462,999, 5,616,661 and 5,668,228 all of which are fully incorporated herein by reference.)

The reactor pressure in a gas phase process may vary from about 10 psig (69 kPa) to about 500 psig (3448 kPa), preferably from about 100 psig (690 kPa) to about 500 psig (3448 kPa), preferably in the range of from about 200 psig (1379 kPa) to about 400 psig (2759 kPa), more preferably in the range of from about 250 psig (1724 kPa) to about 350 psig (2414 kPa).

The reactor temperature in the gas phase process may vary from about 30° C. to about 120° C., preferably from about 60° C. to about 115° C., more preferably in the range of from about 70° C. to 110° C., and most preferably in the range of from about 70° C. to about 95° C. In another embodiment when high density polyethylene is desired then the reactor temperature is typically between 70 and 105° C.

The productivity of the catalyst system in a gas phase system is influenced by the partial pressure of the main monomer. The preferred mole percent of the main monomer, ethylene or propylene, preferably ethylene, is from about 25 to 90 mole percent and the comonomer partial pressure is in the range of from about 138 kPa to about 517 kPa, preferably about 517 kPa to about 2069 kPa, which are typical conditions in a gas phase polymerization process. Also in some systems the presence of comonomer can increase productivity.

In a preferred embodiment, the reactor utilized in the present invention is capable of producing more than 500 lbs of polymer per hour (227 Kg/hr) to about 200,000 lbs/hr (90,900 Kg/hr) or higher, preferably greater than 1000 lbs/hr (455 Kg/hr), more preferably greater than 10,000 lbs/hr (4540 Kg/hr), even more preferably greater than 25,000 lbs/hr (11,300 Kg/hr), still more preferably greater than 35,000 lbs/hr (15,900 Kg/hr), still even more preferably greater than 50,000 lbs/hr (22,700 Kg/hr) and preferably greater than 65,000 lbs/hr (29,000 Kg/hr) to greater than 100,000 lbs/hr (45,500 Kg/hr), and most preferably over 100,000 lbs/hr (45,500 Kg/hr).

Other gas phase processes contemplated by the process of the invention include those described in U.S. Pat. Nos. 5,627,242, 5,665,818 and 5,677,375, and European publications EP-A-0 794 200, EP-A-0 802 202 and EP-B-634 421 all of which are herein fully incorporated by reference.

In another preferred embodiment the catalyst system in is liquid form and is introduced into the gas phase reactor into a resin particle lean zone. For information on how to introduce a liquid catalyst system into a fluidized bed polymerization into a particle lean zone, please see U.S. Pat. No. 5,693,727, which is incorporated by reference herein.

Slurry Phase Polymerization

A slurry polymerization process generally operates between 1 to about 50 atmosphere pressure range (15 psi to 735 psi, 103 kPa to 5068 kPa) or even greater and temperatures in the range of 0° C. to about 120° C. In a slurry polymerization, a suspension of solid, particulate polymer is formed in a liquid polymerization diluent medium to which monomer and comonomers along with catalyst are added. The suspension including diluent is intermittently or continuously removed from the reactor where the volatile components are separated from the polymer and recycled, optionally after a distillation, to the reactor. The liquid diluent employed in the polymerization medium is typically an alkane having from 3 to 7 carbon atoms, preferably a branched alkane. The medium employed should be liquid under the conditions of polymerization and relatively inert. When a propane medium is used the process must be operated above the reaction diluent critical temperature and pressure. Preferably, a hexane or an isobutane medium is employed.

In one embodiment, a preferred polymerization technique of the invention is referred to as a particle form polymerization, or a slurry process where the temperature is kept below the temperature at which the polymer goes into solution. Such technique is well known in the art, and described in for instance U.S. Pat. No. 3,248,179 which is fully incorporated herein by reference. The preferred temperature in the particle form process is within the range of about 85° C. to about 110° C. Two preferred polymerization methods for the slurry process are those employing a loop reactor and those utilizing a plurality of stirred reactors in series, parallel, or combinations thereof. Non-limiting examples of slurry processes include continuous loop or stirred tank processes. Also, other examples of slurry processes are described in U.S. Pat. No. 4,613,484, which is herein fully incorporated by reference.

In another embodiment, the slurry process is carried out continuously in a loop reactor. The catalyst, as a slurry in isobutane or as a dry free flowing powder, is injected regularly to the reactor loop, which is itself filled with circulating slurry of growing polymer particles in a diluent of isobutane containing monomer and comonomer. Hydrogen, optionally, may be added as a molecular weight control. The reactor is maintained at a pressure of 3620 kPa to 4309 kPa and at a temperature in the range of about 60° C. to about 104° C. depending on the desired polymer melting characteristics. Reaction heat is removed through the loop wall since much of the reactor is in the form of a double-jacketed pipe. The slurry is allowed to exit the reactor at regular intervals or continuously to a heated low pressure flash vessel, rotary dryer and a nitrogen purge column in sequence for removal of the isobutane diluent and all unreacted monomer and comonomers. The resulting hydrocarbon free powder is then compounded for use in various applications.

In another embodiment, the reactor used in the slurry process of the invention is capable of and the process of the invention is producing greater than 2000 lbs of polymer per hour (907 Kg/hr), more preferably greater than 5000 lbs/hr (2268 Kg/hr), and most preferably greater than 10,000 lbs/hr (4540 Kg/hr). In another embodiment the slurry reactor used in the process of the invention is producing greater than 15,000 lbs of polymer per hour (6804 Kg/hr), preferably greater than 25,000 lbs/hr (11,340 Kg/hr) to about 100,000 lbs/hr (45,500 Kg/hr).

In another embodiment in the slurry process of the invention the total reactor pressure is in the range of from 400 psig (2758 kPa) to 800 psig (5516 kPa), preferably 450 psig (3103 kPa) to about 700 psig (4827 kPa), more preferably 500 psig (3448 kPa) to about 650 psig (4482 kPa), most preferably from about 525 psig (3620 kPa) to 625 psig (4309 kPa).

In yet another embodiment in the slurry process of the invention the concentration of predominant monomer in the reactor liquid medium is in the range of from about 1 to 10 weight percent, preferably from about 2 to about 7 weight percent, more preferably from about 2.5 to about 6 weight percent, most preferably from about 3 to about 6 weight percent.

Another process of the invention is where the process, preferably a slurry or gas phase process is operated in the absence of or essentially free of any scavengers, such as triethylaluminum, trimethylaluminum, tri-isobutylaluminum and tri-n-hexylaluminum and diethyl aluminum chloride, dibutyl zinc and the like. This process is described in PCT publication WO 96/08520 and U.S. Pat. No. 5,712,352, which are herein fully incorporated by reference.

In another embodiment the process is run with scavengers. Typical scavengers include trimethyl aluminum, tri-isobutyl aluminum and an excess of alumoxane or modified alumoxane.

Homogeneous, Bulk or Solution Phase Polymerization

The polymer may be made advantageously by the continuous solution polymerization process described in WO 02/34795, advantageously in a single reactor and separated by liquid phase separation from the alkane solvent.

The catalysts described herein can be used advantageously in homogeneous solution processes. Generally this involves polymerization in a continuous reactor in which the polymer formed and the starting monomer and catalyst materials supplied, are agitated to reduce or avoid concentration gradients. Suitable processes operate above the melting point of the polymers at high pressures, from 1 to 3000 bar (10–30,000 MPa), in which the monomer acts as diluent or in solution polymerization using a solvent.

Temperature control in the reactor is obtained by balancing the heat of polymerization and with reactor cooling by reactor jackets or cooling coils to cool the contents of the reactor, auto refrigeration, pre-chilled feeds, vaporization of liquid medium (diluent, monomers or solvent) or combinations of all three. Adiabatic reactors with pre-chilled feeds may also be used. The reactor temperature depends on the catalyst used. In general, the reactor temperature preferably can vary between about 0° C. and about 160° C., more preferably from about 10° C. to about 140° C., and most preferably from about 40° C. to about 120° C. In series operation, the second reactor temperature is preferably higher than the first reactor temperature. In parallel reactor operation, the temperatures of the two reactors are independent. The pressure can vary from about 1 mm Hg to 2500 bar (25,000 MPa), preferably from 0.1 bar to 1600 bar (1–16,000 MPa), most preferably from 1.0 to 500 bar (10–5000 MPa).

Each of these processes may also be employed in single reactor, parallel or series reactor configurations. The liquid processes comprise contacting olefin monomers with the above described catalyst system in a suitable diluent or solvent and allowing said monomers to react for a sufficient time to produce the desired polymers. Hydrocarbon solvents are suitable, both aliphatic and aromatic. Alkanes, such as hexane, pentane, isopentane, and octane, are preferred.

The process can be carried out in a continuous stirred tank reactor, batch reactor or plug flow reactor, or more than one reactor operated in series or parallel. These reactors may have or may not have internal cooling and the monomer feed my or may not be refrigerated. See the general disclosure of U.S. Pat. No. 5,001,205 for general process conditions. See also, international application WO 96/33227 and WO 97/22639. All documents are incorporated by reference for US purposes for description of polymerization processes, metallocene selection and useful scavenging compounds.

Polymers Produced, Applications and Formulations of the Polymers

The polymers produced herein, particularly the propylene homopolymers and copolymers, may have a weight average molecular weight (Mw) of 25,000 to 500,000. The polymers produced herein, particularly the propylene homopolymers and copolymers, may have a molecular weight distribution (Mw/Mn) of up to 5, more preferably of up to 4 more preferably from 1.1 to 3, more preferably from 1.1 to 2.

In a preferred embodiment the polymers produced herein have a Mw of from 10,000 to 1,000,000, preferably 50,000 to 500,000, more preferably 100,000. In other embodiments Mw's of 10,000 or less are produced.

Any of the polymer compositions produced by this invention may be functionalized. Preferred functional groups include maleic acid and maleic anhydride. By functionalized is meant that the polymer has been contacted with an unsaturated acid or anhydride. Preferred unsaturated acids or anhydrides include any unsaturated organic compound containing at least one double bond and at least one carbonyl group. Representative acids include carboxylic acids, anhydrides, esters and their salts, both metallic and non-metallic. Preferably the organic compound contains an ethylenic unsaturation conjugated with a carbonyl group (—C=O). Examples include maleic, fumaric, acrylic, methacrylic, itaconic, crotonic, alpha-methyl crotonic, and cinnamic acids as well as their anhydrides, esters and salt derivatives. Maleic anhydride is particularly preferred. The unsaturated acid or anhydride is preferably present at about 0.1 weight % to about 10 weight %, preferably at about 0.5 weight % to about 7 weight %, even more preferably at about 1 to about 4 weight %, based upon the weight of the hydrocarbon resin and the unsaturated acid or anhydride.

The polymers produced herein may be used in film, molding, barrier applications. In a particular embodiment, the polymers produced herein are blown, molded, cast or otherwise formed into films. In a particularly preferred embodiment the polymers produced herein are formed into plastic bags.

Tests

Molecular weights (weight average molecular weight (Mw) and number average molecular weight (Mn)) are determined using a Waters 150 Size Exclusion Chromatograph (SEC) equipped with a differential refractive index detector (DRI), an online low angle light scattering (LALLS) detector and a viscometer (VIS). The details of the detector calibrations have been described elsewhere [Reference: T. Sun, P. Brant, R. R. Chance, and W. W. Graessley, *Macromolecules*, Volume 34, Number 19, 6812–6820, (2001)]; attached below are brief descriptions of the components.

The SEC with three Polymer Laboratories PLgel 10 mm Mixed-B columns, a nominal flow rate 0.5 cm$^3$/min, and a nominal injection volume 300 μL is common to both detector configurations. The various transfer lines, columns and differential refractometer (the DRI detector, used mainly to determine eluting solution concentrations) are contained in an oven maintained at 135° C.

The LALLS detector is the model 2040 dual-angle light scattering photometer (Precision Detector Inc.). Its flow cell, located in the SEC oven, uses a 690 nm diode laser light source and collects scattered light at two angles, 15° and 90°. Only the 15° output was used in these experiments. Its signal is sent to a data acquisition board (National Instruments) that accumulates readings at a rate of 16 per second. The lowest four readings are averaged, and then a proportional signal is sent to the SEC-LALLS-VIS computer. The LALLS detector is placed after the SEC columns, but before the viscometer.

The viscometer is a high temperature Model 150R (Viscotek Corporation). It consists of four capillaries arranged in a Wheatstone bridge configuration with two pressure transducers. One transducer measures the total pressure drop across the detector, and the other, positioned between the two sides of the bridge, measures a differential pressure. The specific viscosity for the solution flowing through the viscometer is calculated from their outputs. The viscometer is inside the SEC oven, positioned after the LALLS detector but before the DRI detector.

Solvent for the SEC experiment was prepared by adding 6 grams of butylated hydroxy toluene (BHT) as an antioxidant to a 4 liter bottle of 1,2,4 Trichlorobenzene (TCB) (Aldrich Reagent grade) and waiting for the BHT to solubilize. The TCB mixture was then filtered through a 0.7 μm glass pre-filter and subsequently through a 0.1 μm Teflon filter. There was an additional online 0.7 μm glass pre-filter/ 0.22 μm Teflon filter assembly between the high pressure pump and SEC columns. The TCB was then degassed with an online degasser (Phenomenex, Model DG-4000) before entering the SEC.

Polymer solutions were prepared by placing dry polymer in a glass container, adding the desired amount of TCB, then heating the mixture at 160° C. with continuous agitation for about 2 hours. All quantities were measured gravimetrically. The TCB densities used to express the polymer concentration in mass/volume units are 1.463 g/ml at room temperature and 1.324 g/ml at 135° C. The injection concentration ranged from 1.0 to 2.0 mg/ml, with lower concentrations being used for higher molecular weight samples.

Prior to running each sample the DRI detector and the injector were purged. Flow rate in the apparatus was then increased to 0.5 ml/minute, and the DRI was allowed to stabilize for 8–9 hours before injecting the first sample. The argon ion laser was turned on 1 to 1.5 hours before running samples by running the laser in idle mode for 20–30 minutes and then switching to full power in light regulation mode.

EXAMPLES

Experimental:

Preparation of N-Mesityl, N'-Benzyl-ethylenediamine:

A mixture of N-Benzyl-ethylenediamine (9.62 g, 64.04 mmol), Mesitylbromide (12.75 g, 64.04 mmol), tris(dibenzylideneacetone)dipalladium (0.15 g, 0.16 mmol), rac-2,2'-bis(diphenylphosphino)-1,1'-binaphthyl (0.30 g, 0.48 mmol), sodium-tert-butoxide (9.20 g, 96 mmol) and toluene (ca. 125 mL) were heated at 110° C. for ca. 40 hours under a nitrogen atmosphere. The reaction mixture was poured into water (100 mL) and the resulting mixture was extracted with ether (3×50 mL). The organic fraction was collected, washed once with brine (100 mL), dried over $MgSO_4$ and the solvent was removed under reduced pressure. The residue was distilled (190° C., 60 mtorr) giving N-mesityl, N'-benzyl-ethylenediamine as a pale yellow liquid (12.5 g).

Preparation of [2-tBu,4-Me-6-$CH_2N(Bz)CH_2CH_2NH$(2,4,6-$Me_3C_6H_2$)$C_6H_2OH$]("PAA-$H_2$")

A mixture of N-Mesityl, N'-benzyl-ethylenediamine (3.0 g, 11.17 mmol), paraformaldehyde (0.34 g, 11.17 mmol), 2-tert-butyl,4-methyl-phenol (1.84 g, 11.18 mmol) and ethanol (4 mL) were heated in a sealed glass ampoule at 110° C. for 15 hours. Water (50 mL) was added and the mixture was extracted with ether (3×75 mL). The combined ether extracts were collected, dried over $MgSO_4$, filtered and the ether removed under reduced pressure giving an orange oil. The orange oil was stirred with ethanol (15 mL) for 1 hour producing a white solid which was collected by filtration, washed with ethanol (3×10 mL) and dried under reduced pressure to give PAA-$H_2$ as a white solid (2.30 g).

Preparation of [2-Ph, 4-Me-6-$CH_2N(Bz)CH_2CH_2NH$(2,4,6-$Me_3C_6H_2$)$C_6H_2OH$]) ("PhPAA-$H_2$")

A mixture of N-Mesityl, N'-benzyl-ethylenediamine (6.23 g, 23.20 mmol), paraformaldehyde (0.70 g, 23.20 mmol), 2-phenyl, 4-methyl-phenol (5.25 g, 23.20 mmol) and ethanol (10 mL) were heated in a sealed glass ampoule at 110° C. for 22 hours. The solvent was removed from the mixture under reduced pressure giving an oily residue which was extracted into $Et_2O$ (ca. 60 mL) and concentrated until a solid precipitates. Pentane (ca. 20 mL) was added to the mixture and a white solid was collected by filtration, washed with pentane (2×20 mL) and dried under reduced pressure giving PhPAA-$H_2$ (8.0 g).

Preparation of [2-(9-$C_{14}H_9$), Me-6-$CH_2N(Bz)CH_2CH_2NH$ (2,4,6-$Me_3C_6H_2$)$C_6H_2OH$]) ("AnthPAA-$H_2$").

A mixture of N-Mesityl, N'-benzyl-ethylenediamine (0.47 g, 1.76 mmol), paraformaldehyde (0.053 g, 1.76 mmol), 2-(9-anthracenyl)-4-methyl-phenol (0.50 g, 1.76 mmol) and ethanol (4 mL) were heated in a sealed glass ampoule at 110° C. for 14 hours. The mixture was cooled to room temperature, 20 mL of EtOH was added and the mixture was stirred. A white solid formed and was collected by filtration, washed with EtOH (2×10 mL) and dried under reduced pressure to give AnthPAA-$H_2$ (0.38 g).

Preparation of [2-($CH_2N(Bz)CH_2CH_2NH$(2,4,6-$Me_3C_6H_2$)-1-$C_{10}H_6OH$] ("NapAA-$H_2$")-adapted from. Bull. Korean Chem. Soc. 1999, 20, 973.

A mixture of N-Mesityl, N'-benzyl-ethylenediamine (1.23 g, 4.58 mmol), paraformaldehyde (0.14 g, 4.67 mmol), 1-napthol (0.55 g, 3.81 mmol) and toluene (ca. 20 mL) were heated in a sealed glass ampoule at 85° C. for 20 hours. The resulting brown residue was extracted into hexane-$Et_2O$ (1:1, ca. 50 mL) and the solution was washed with water (50 mL). The organic layer was collected, dried over $MgSO_4$, filtered and the solvents removed under a stream of nitrogen leaving a brown oil which was crystallized from a EtOH-$Et_2O$ mixture giving NapAA-$H_2$ as a white solid (0.40 g).

Preparation of [2-tBu,4-Me-6-(($CH_2N(Bz)CH_2CH_2N$(2,4,6-$Me_3C_6H_2$))$C_6H_2O$]Hf($CH_3$)$_2$ (PAA-HfMe$_2$).

To a slurry of PAA-$H_2$ (0.75 g, 1.68 mmol) in pentane (5 mL) was added a solution of Hf(NMe$_2$)$_4$ (0.60 g, 1.68 mmol) in pentane (10 mL). The mixture was stirred for 20 minutes and the solvent removed under reduced pressure giving PAAHf(NMe$_2$)$_2$ as a white solid, which was identified by $^1$H NMR. A solution PAAHf(NMe$_2$)$_2$ (0.40 g,) in toluene (10 mL) was treated with excess trimethylsilylchloride (ca. 2 mL) and stirred overnight resulting in the formation of a white solid. The white solid was collected by filtration, washed with pentane and dried under reduced pressure giving PAAHfCl$_2$ (0.32 g) which was identified by $^1$H NMR. A slurry of PAAHfCl$_2$ (0.32 g, 0.43 mmol) in ether (10 mL) was cooled to ca. −80° C. and treated with methyl lithium (0.62 mL of 1.4 M solution in ether, 0.87 mmol), stirred for 5 minutes cold then stirred for one hour at room temperature. The solvent was removed from the mixture under reduced pressure giving a white solid which was extracted into pentane (70 mL), filtered and concentrated to ca. 10 mL to produce a white precipitate. The precipitate was collected by filtration and dried under reduced pressure giving PAA-HfMe$_2$ as a white solid (0.11 g).

Preparation of [2-tBu,4-Me-6-(($CH_2N(Bz)CH_2CH_2N$(2,4,6-$Me_3C_6H_2$))$C_6H_2O$]Ti($CH_2Ph$)$_2$ (PAA-TiBz$_2$).

A solution of PAA-$H_2$ (0.32 g, 0.73 mmol) in toluene (ca. 7 mL) was added to a solution of tetrabenzyltitanium (0.32 g, 0.72 mmol) in toluene (ca. 5 mL) at room temperature.

The deep-red mixture was stirred for 30 minutes then the solvent was removed under reduced pressure. The residue was washed with pentane (3×10 mL) and dried under reduced pressure giving as a brick-red solid (0.21 g).

Preparation of [2-tBu,4-Me-6-((CH$_2$N(Bz)CH$_2$CH$_2$N(2,4,6-Me$_3$C$_6$H$_2$))C$_6$H$_2$O]Zr(CH$_2$Ph)$_2$ (PAA-ZrBz$_2$)

Toluene (8 mL) was added to a stirred mixture of PAA-H$_2$ (0.99 g, 2.22 mmol) and tetrabenzylzirconium (1.01 g, 2.22 mmol) and stirring was continued for 15 minutes. The solvent was removed under reduced pressure leaving a tan glassy solid which was stirred with pentane (10 mL) for several hours producing a white solid. The white solid was collected by filtration and washed with pentane (2×5 mL) and dried under reduced pressure giving PAA-ZrBz$_2$ (1.18 g).

Preparation of [2-tBu,4-Me-6-((CH$_2$N(Bz)CH$_2$CH$_2$N(2,4,6-Me$_3$C$_6$H$_2$))C$_6$H$_2$O]HfBz$_2$ (PAA-HfBz$_2$)

To a stirred slurry of tetrabenzylhafnium (0.52 g, 0.96 mmol) in toluene (10 mL) was added PAA-H$_2$ (0.43 g, 0.96 mmol) as a solution in toluene (10 mL), and the mixture was stirred for one hour. The solvent was removed under reduced pressure leaving a tan glassy solid which was stirred with pentane (10 mL) producing a white solid. The white solid was collected by filtration, washed with pentane (10 mL) and dried under reduced pressure to give PAA-HfBz$_2$ (0.53 g).

Preparation of [2-Ph, 4-Me-6-CH$_2$N(Bz)CH$_2$CH$_2$NH(2,4,6-Me$_3$C$_6$H$_2$)C$_6$H$_2$OH]Ti(CH$_2$Ph)$_2$ (PhPAATiBz$_2$).

A solution of PhPAA-H$_2$ (0.50 g, 1.0 mmol) in toluene (ca. 10 mL) was added to a solution of tetrabenzyltitanium (0.41 g, 1.0 mmol) in toluene (ca. 8 mL) at room temperature and the mixture was stirred for 30 minutes. The mixture as filtered and the solvent was removed under reduced pressure to give a red oil. Pentane (ca. 15 mL) was added to the oil producing a brick-red solid which was washed with pentane (3×10 mL) and dried under reduced pressure giving PhPAATiBz$_2$ (0.48 g).

Preparation of [2-Ph, 4-Me-6-CH$_2$N(Bz)CH$_2$CH$_2$NH(2,4,6-Me$_3$C$_6$H$_2$)C$_6$H$_2$OH]Zr(CH$_2$Ph)$_2$ (PhPAAZrBz$_2$).

Toluene (ca. 15 mL) was added to as stirred mixture of tetrabenzylzirconium (0.42 g, 0.92 mmol) and (0.47 g, 0.93 mmol). After stirring 2 hours at room temperature, the solvent was removed under a stream of nitrogen leaving a sticky solid which was stirred with pentane (ca. 20 mL) to give an off-white solid. The solid was washed with pentane (3×10 mL) and dried under reduced pressure giving PhPAAZrBz$_2$ (0.42 g).

Preparation of [2-Ph, 4-Me-6-CH$_2$N(Bz)CH$_2$CH$_2$NH(2,4,6-Me$_3$C$_6$H$_2$)C$_6$H$_2$OH]Hf(CH$_2$Ph)$_2$ (PhPAAHfBz$_2$).

A solution of tetrabenzylhafnium (0.19 g, 0.35 mmol) in toluene (ca.4 mL) was added to a solution of PhPAA-H$_2$ (0.17 g, 0.35 mmol) in toluene (ca. 10 mL) at room temperature and the mixture was stirred for 1 hour. The mixture as filtered and the solvent was removed under a stream of nitrogen to give a yellow oil. Pentane (ca. 10 mL) was added to the oil producing a white solid which was washed with pentane (2×5 mL) and dried under erduced pressure giving PhPAAHfBz$_2$ (0.16 g).

Preparation of [2-tBu,4-Me-6-CH$_2$N(Bz)CH$_2$CH$_2$N(2,4,6-Me$_3$C$_6$H$_2$)C$_6$H$_2$O]Zr(CH$_2$Ph)$_2$(AnthPAAZrBz$_2$)

A solution of Zr(Ch2Ph)4 (0.15 g, 0.33 mmol) was added to a stirred slurry of AnthPAA-H$_2$ (0.18 g, 0.33 mmol) at room temperature. After stirring for 30 minutes, the solvent was removed under reduced pressure to leave a white-yellow solid which was washed with pentane (3×20 mL) and dried under reduced pressure giving AnthPAAZrBz$_2$ (0.18 g).

Preparation of [2-tBu,4-Me-6-CH$_2$N(Bz)CH$_2$CH$_2$N(2,4,6-Me$_3$C$_6$H$_2$)C$_6$H$_2$O]Hf(CH$_2$Ph)$_2$ (AnthPAAHfBz$_2$)

A solution of Hf(CH$_2$Ph)$_4$ (0.21 g, 0.38 mmol) in toluene (ca. 10 mL) was added to a stirred slurry of AnthPAA-H$_2$ (0.21 g, 0.38 mmol) in toluene (ca.5 mL) at room temperature. After stirring for 30 minutes, the solvent was removed under reduced pressure leaving a white-yellow solid which was washed with pentane (3×20 mL) and dried under reduced pressure giving AnthPAAHfBz$_2$ (0.25 g).

Preparation of [2-(CH$_2$N(Bz)CH$_2$CH$_2$NH(2,4,6-Me$_3$C$_6$H$_2$)-1-C$_{10}$H$_6$OH]Zr(CH$_2$Ph)$_2$ (NapAAZrBz$_2$).

A solution of NAPAA-H$_2$ (0.13 g, 0.31 mmol) in toluene (ca. 10 mL) was added to a solution of tetrabenzylzirconium (0.14 g, 0.31 mmol) in toluene (ca. 10 mL) at room temperature and the mixture was stirred for 1 hour. The mixture was filtered and the solvent removed under a stream of nitrogen leaving a light yellow solid which was washed with pentane (3×10 mL) giving NapAAZrBz$_2$ as a white solid (0.07g).

Preparation of [2-(CH$_2$N(Bz)CH$_2$CH$_2$NH(2,4,6-Me$_3$C$_6$H$_2$)-1-C$_{10}$H$_6$OH]Hf(CH$_2$Ph)$_2$ (NapAAHfBz$_2$).

A solution of NAPAA-H$_2$ (0.13 g, 0.31 mmol) in toluene (ca. 10 mL) was added to a solution of tetrabenzylhafnium (0.17 g, 0.31 mmol) in toluene (ca. 10 mL) at room temperature and the mixture was stirred for 45 minutes. The solvent removed under a stream of nitrogen and the resulting oil was stirred with pentane (ca. 5 mL) to produce a white solid which was washed with pentane (3×10 mL) giving NapAAHfBz$_2$ (0.11 g).

Polymerization Reagents 1-hexene (97%) and 1-octene (98%) (Aldrich Chemical Company) are degassed by purging with nitrogen overnight and dried by stirring over NaK overnight followed by filtration through basic alumina (Aldrich Chemical Company, Brockman Basic 1) under nitrogen. Solvents, like toluene and hexanes, and ethylene(polymerization grade) were purified by passing through a series of columns: 500 cc Oxyclear cylinder from Labclear (Oakland, Calif.) followed by a 500 cc column packed with dried 3 Å mole sieves purchased from Aldrich Chemical Company, and a 500 cc column packed with dried 5 Å mole sieves (Aldrich Chemical Company). Polymerization grade propylene is used without further purification. MAO (methylalumoxane, 10 wt % in toluene) from Albemarle Corporation and TNOA (tri-n-octylaluminum, neat) from AKZO Nobel were used as received. Tris(perfluorphenyl) boron (B(pfp)$_3$, B(C$_6$F$_5$)$_3$) from Boulder Scientific Company was sublimed before use. Dimethylanilinium tetrakis(perfluorophenyl)borate ([DMAH][B(pfp)$_4$], [PhNMe$_2$H][B(C$_6$F$_5$)$_4$]) was purchased from Albemarle Corporation and used without further purification.

Ethylene-Octene Copolymerizations

All polymerizations were performed in a "triplicate series" in which three individual experiments are performed simultaneously under conditions that are identical to within the detection limits of the equipment. The results from each triplicate series are reported together, including statistical averages and standard deviations. Polymerizations were performed in a glass-lined 5-milliliter autoclave reactor equipped with a mechanical stirrer, an external heater for temperature control, a septum inlet and a regulated supply of dry nitrogen and ethylene in an inert atmosphere (Nitrogen) glove box. The reactor was dried and degassed thoroughly at 115° C. The hexane diluent, comonomer, and scavenger, were added at room temperature in a nitrogen filled glovebox. The reactor was then brought to process pressure and charged with ethylene while stirring at 800 RPM. The activator and catalyst were added via syringe with the reactor at process conditions. Details of the reagents and addition sequence for specific polymerizations are as follows:

Polymerizations 1 & 2:
Octene (197 μL), hexane (4.0 mL), tri-n-octylaluminum (100 μL of a 0.01 M solution in hexane), catalysts (100 μL of a 1 mM solution in toluene) and activator (100 μL of a 1 mM solution in toluene).

Polymerizations 3–13:
Octene (100 μL neat), followed by a hexane chaser (0.5 mL), tri-n-octylaluminum (100 μL of a 0.10 M solution on toluene), followed by a hexane chaser (0.5 mL), activator (for activators A and B, 200 μL of a 1 mM solution in toluene, or for MAO 450 μL of a 1.5% wt solution in toluene) followed by a hexane chaser (0.5 mL) and catalyst (200 μL of a 1 mM solution in toluene) followed by a hexane chaser (0.1 mL).

The polymerization was continued while maintaining the reaction vessel within 3° C. of the target process temperature and 5 psig of target process pressure (by automatic addition of ethylene on demand) until a fixed uptake of ethylene was noted (corresponding to ca. 0.20 g polymer) or until a maximum reaction time of 30 minutes had passed. The reaction was stopped by pressurizing the reactor to 30 psig above the target process pressure with a gas mixture composed of 5 mol % Oxygen in Argon. The polymer was recovered by vacuum centrifugation of the reaction mixture. Selected data is summarized below.

Polymerization Conditions: Hexane Solvent.
Note: A=[PhN(H)Me$_2$][(C$_6$F$_5$)$_4$B]; B=[Ph$_3$C][(C$_6$F$_5$)$_4$B]. (Ph is phenyl); PDI is Mw/Mn.

Propylene Polymerizations

All polymerizations were performed in a "triplicate series" in which three individual experiments are performed simultaneously under conditions that are identical to within the detection limits of the equipment. The results from each triplicate series are reported together, including statistical averages and standard deviations. Propylene Polymerizations were performed in glass-lined 22.5 mL reactors equipped with disposable PEEK mechanical stirrers, an external heater for temperature control, septum inlet and regulated supply of nitrogen, ethylene, and propylene in an inert atmosphere of Nitrogen glove box. The reactor was dried and degassed at 115° C. for 5 hours and then purged with nitrogen at room temperature for another five hours, then cooled to room temperature. Sequentially, propylene (4 mL), a hexane chaser (0.1 mL), tri-n-octylaluminum (100 μL of a 0.01M solution in hexane) and a hexane chaser (0.5 mL) were added at room temperature. The reactor was heated to process temperature 70° C. while stirring at 800 rpm. The activator (200 μL of a 1 mmol/L solution in toluene for activators A and B, or 450 μL of a 1.5% wt toluene solution of MAO) were added followed by a hexane chaser (0.5 mL). The catalyst (200 μL of a 1 mmol/L solution in toluene), was injected at process conditions followed by a 1 mL hexane chaser. The reaction was run to a predetermined drop in pressure (~5 psi) or for 30 minutes, at the end of which it was quenched with 5 mol % Oxygen in Argon. The reactor was then cooled, vented and the polymer recovered by vacuum centrifugation of the reaction mixture. The polymer was characterized by GPC and, in one case, $^{13}$C NMR to determine the tacticity of the resultant polypropylene.

All documents described herein are incorporated by reference herein, including any priority documents and/or testing procedures. As is apparent from the foregoing general description and the specific embodiments, while forms of the invention have been illustrated and described, various modifications can be made without departing from the spirit and scope of the invention. Accordingly, it is not intended that the invention be limited thereby.

Ethylene-octene Copolymerizations:

| Catalyst | Temp (C.) | P(psi) | Activator | Mw(K) | PDI | wt % octene | activity (g polymer/ mmol cat hr) |
|---|---|---|---|---|---|---|---|
| 1. PAA-ZrBz2 | 60 | 109 | A | 11065 | 2.2 | 21 | 3650 |
| | | | | 7326 | 1.5 | 16 | 4039 |
| | | | | 7619 | 1.6 | 22 | 4765 |
| | | | Ave (std dev.) | 8670 (2079) | 1.8 (0.4) | 20 (3) | 4151 (566) |
| 2. PPA-ZrBz2 | 60 | 109 | B | 10067 | 1.9 | 20 | 4865 |
| | | | | 15568 | 3.1 | 18 | 4256 |
| | | | | 9748 | 2.0 | 18 | 4410 |
| | | | Ave (std dev.) | 11794 (3272) | 2.3 (0.7) | 19 (1) | 4510 (317) |
| 3. PAA-TiBz2 | 60 | 109 | A | 149298 | 1.6 | 5 | 238 |
| | | | | 170989 | 1.6 | 4 | 246 |
| | | | | 167026 | 1.7 | 5 | 244 |
| | | | Ave (std dev.) | 162438 (11550) | 1.6 (0.1) | 5 (0) | 243 (4) |
| 4. PhPAA-TiBz2 | 60 | 109 | A | 3439084 | 1.5 | 6 | 668 |
| | | | | 3476680 | 1.6 | 6 | 647 |
| | | | | 3451755 | 1.5 | 6 | 660 |
| | | | Ave (std dev.) | 3455840 (19128) | 1.5 (0) | 6 (0) | 658 (11) |

-continued

| Catalyst | Temp (C.) | P(psi) | Activator | Mw(K) | PDI | wt % octene | activity (g polymer/ mmol cat hr) |
|---|---|---|---|---|---|---|---|
| 5. PhPAA-ZrBz2 | 60 | 109 | A | 3112382 | 2.0 | 7 | 698 |
| | | | | 3368995 | 1.9 | 9 | 721 |
| | | | | 3383687 | 1.8 | 8 | 655 |
| | | | Ave (std dev.) | 3288355 (152547) | 1.9 (0.1) | 8 (1) | 691 (34) |
| 6. PAA-TiBz2 | 60 | 400 | A | 374388 | 2.0 | 2 | 6455 |
| | | | | 426059 | 2.1 | 2 | 8059 |
| | | | | 387141 | 1.9 | 3 | 7627 |
| | | | Ave (std dev.) | 395863 (26917) | 2 (0.1) | 2 (0) | 7380 (830) |
| 7. PhPAA-ZrBz2 | 60 | 400 | A | 5990 | 1.5 | 16 | 11177 |
| | | | | 5620 | 1.5 | 14 | 10876 |
| | | | | 6001 | 1.5 | 21 | 11179 |
| | | | Ave (std dev.) | 5870 (217) | 1.5 (0) | 17 (4) | 11077 (174) |
| 8. PhPAA-ZrBz2 | 60 | 400 | B | 5185 | 1.4 | 19 | 3736 |
| | | | | 5529 | 1.5 | 12 | 2981 |
| | | | | 5640 | 1.5 | 25 | 6853 |
| | | | Ave (std dev.) | 5451 (237) | 1.5 (0) | 19 (7) | 4523 (2053) |
| 9. NapAA-ZrBz2 | 60 | 400 | A | 6840 | 1.6 | 8 | 2510 |
| | | | | 6243 | 1.6 | 8 | 2270 |
| | | | | 6636 | 1.6 | 8 | 2104 |
| | | | Ave (std dev.) | 6573 (303) | 1.6 (0) | 8 (0) | 2295 (204) |
| 10. PAA-TiBz2 | 60 | 400 | B | 925994 | 3.0 | 3 | 6940 |
| | | | | 786817 | 2.8 | 4 | 372 |
| | | | | 451641 | 2.1 | 2 | 1434 |
| | | | Ave (std dev.) | 721484 (243832) | 2.6 (0.5) | 3 (1) | 2915 (3526) |
| 11. PhPAA-TiBz2 | 105 | 109 | A | 1032828 | 4.9 | 12 | 279 |
| | | | | 1040111 | 4.1 | 12 | 300 |
| | | | | 564068 | 2.5 | 14 | 363 |
| | | | Ave (std dev.) | 879002 (272765) | 3.8 (1.2) | 13 (1) | 314 (44) |
| 12. NapAA-HfBz2 | 105 | 109 | B | 1184124 | 18.9 | 8 | 394 |
| | | | | 1203675 | 16.7 | 10 | 439 |
| | | | | 1050983 | 16.0 | 9 | 445 |
| | | | Ave (std dev.) | 1146261 (83090) | 17 (2) | 9 (1) | 426 (28) |
| 13. PhPAA-TiBz2 | 105 | 109 | MAO | 483523 | 10.2 | 5 | 264 |
| | | | | 481831 | 6.6 | 5 | 253 |
| | | | | 525061 | 6.6 | 5 | 292 |
| | | | Ave (std dev.) | 496805 (24485) | 7.8 (2.1) | 5 (0) | 270 (20) |

Propylene Polymerizations:

| Catalyst | Temp (C.) | Activator | Mw(K) | PDI | activity (g polymer/ mmol cat hr) | Tacticity* (mole fraction) |
|---|---|---|---|---|---|---|
| PhPAA-ZrBz2 | 70 | A | 7571 | 2.0 | 461 | mmmm = 0.038 |
| | | | 7289 | 2.1 | 459 | rrrr = 0.181 |
| | | | 7518 | 2.1 | 414 | *combined polymer from the 3 runs |
| | | ave(std dev.) | 7459 (150) | 2.1 (0.1) | 445 (27) | |

-continued

| Catalyst | Temp (C.) | Activator | Mw(K) | PDI | activity (g polymer/ mmol cat hr) | Tacticity* (mole fraction) |
|---|---|---|---|---|---|---|
| PhPAA-ZrBz2 | 70 | B | 5645 | 2.0 | 201 | |
| | | | 4459 | 1.8 | 206 | |
| | | | 4607 | 1.8 | 218 | |
| | | ave(std dev.) | 4904 (646) | 1.9 (0.1) | 208 (9) | |
| PhPAA-HfBz2 | 70 | A | 4249 | 1.5 | 228 | |
| | | | 4297 | 1.4 | 193 | |
| | | | 4199 | 1.5 | 215 | |
| | | ave(std dev.) | 4248 (49) | 1.5 (0.1) | 212 (18) | |
| NapAA-ZrBz2 | 70 | A | 5172 | 1.5 | 230 | |
| | | | 5632 | 1.5 | 249 | |
| | | | 5679 | 1.5 | 313 | |
| | | ave(std dev.) | 5494 (280) | 1.5 (0) | 264 (43) | |
| NapAA-HfBz2 | 70 | A | 8230 | 2.2 | 227 | |
| | | | 7943 | 2.2 | 238 | |
| | | | 917 | 1.4 | 204 | |
| | | ave(std dev.) | 5697 (4142) | 1.9 (0.5) | 223 (17) | |

The invention claimed is:

1. A catalyst precursor compound comprising a tridentate phenoxy-amide-amine group bound to a group 3, 4, 5, 6, 7, 8, 9, 10, 11 or 12 metal or a lanthanide metal.

2. A catalyst system comprising the catalyst precursor compound of claim 1 and an activator.

3. The catalyst system of claim 2 wherein the activator comprises an alumoxane.

4. A process to polymerize olefins comprising contacting the catalyst system of claim 2 with one or more olefins.

5. The catalyst precursor compound of claim 1, wherein the tridentate phenoxy-amide-amine group is a tridentate thiophenoxy-amide-amine.

6. A catalyst system comprising the catalyst precursor of claim 5 and an activator.

7. The catalyst system of claim 6 wherein the activator comprises an alumoxane.

8. A process to polymerize olefins comprising contacting the catalyst system of claim 6 with one or more olefins.

9. A catalyst precursor composition represented by the formula:

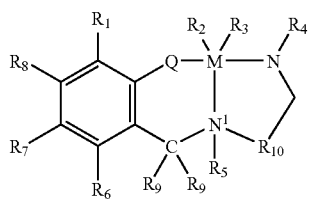

wherein:

M is a group 4 to group 9 transition metal or lanthanide metal, provided however $N^1$ is not part of a pyridine ring when M is a group 8, 9, or 10 metal:

Q is oxygen or sulfur;

N is nitrogen;

$N^1$ is nitrogen;

$R_1$ is a hydrogen, a hydrocarbyl, a substituted hydrocarbyl, a halocarbyl, a substituted halocarbyl, a heteroatom or heteroatom containing group;

$R_2$ and $R_3$ are independently, a hydrogen, a halogen, a hydrocarbyl, a substituted hydrocarbyl, a halocarbyl, or a substituted halocarbyl, a heteroatom or heteratom containing group and $R_2$ and $R_3$ together may form a multidentate ligand, $R_4$ is hydrogen, a hydrocarbyl, a substituted hydrocarbyl, a halocarbyl, a substituted halocarbyl, a heteroatom or heteroatom containing group;

$R_5$ is a hydrogen, a hydrocarbyl, a substituted hydrocarbyl, a halocarbyl, a substituted halocarbyl, a heteroatom or heteroatom containing group;

$R_6$, $R_7$, and $R_8$ are, independently, a hydrogen, a hydrocarbyl, a substituted hydrocarbyl, a halocarbyl, a substituted halocarbyl, a heteroatom or heteroatom containing group, and any two of $R_6$, $R_7$, and $R_8$ may form a fused ring system;

each $R_9$ is, independently, hydrogen, a hydrocarbyl, a substituted hydrocarbyl, a halocarbyl, a substituted halocarbyl group, or a heteroatom or heteroatom containing group;

$R_{10}$ is a hydrocarbyl, a substituted hydrocarbyl, a halocarbyl, a substituted halocarbyl group, or a heteroatom or heteroatom containing group;

where any two adjacent R groups may form a ring structure.

10. The composition of claim 9 where M is a group group 4 to 6 metal.

11. The composition of claim 9 where M is a group 4 metal.

12. The composition of claim 9 where M is Titanium, zirconium or hafnium.

13. The composition of claim 9 where Q is oxygen.

14. The composition of claim 9 where at least one of $R_1$, $R_5$, $R_6$, $R_7$, and $R_8$ is not hydrogen.

15. The composition of claim 9 where at least one of $R_1$, $R_6$, $R_7$, and $R_8$ is not hydrogen.

16. The composition of claim 9 where any two of $R_1$, $R_6$, $R_7$, and $R_8$ are part of a napthol ring.

17. The composition of claim 9 where $R_1$, $R_6$, $R_7$ and $R_8$ are independently, hydrogen, a $C_1$ to $C_{20}$ alkyl group or a $C_6$ to $C_{40}$ aryl group.

18. The composition of claim 9 where $R_1$, $R_6$, $R_7$ and $R_8$ are, independently, a $C_4$ to $C_{20}$ tertiary alkyl group.

19. The composition of claim 9 where $R_1$, $R_6$, $R_7$ and $R_8$ are, independently, butyl, t-butyl, isobutyl, pentyl, hexyl, heptyl, isohexyl, octyl, isooctyl, decyl, nonyl, dodecyl, phenyl, anthracenyl, napthyl, or an isomer thereof, or a heteroatom containing group.

20. The composition of claim 9 where $R_1$, $R_6$, $R_7$ and/or $R_8$ are a heteroatom containing group selected from the group consisting of include imines, amines, oxides, phosphines, ethers, carbonyls, oxazolines, and thioethers.

21. The composition of claim 9 where one or more of $R_1$, $R_6$, $R_7$ and $R_8$ is a pyridine.

22. The composition of claim 9 where $R_5$ is hydrogen, a $C_6$ to $C_{40}$ aryl group, a $C_1$ to $C_{20}$ alkyl group, a benzyl group, a substituted benzyl group, or a heteroatom containing group.

23. The composition of claim 9 where $R_5$ is a heteroatom containing group selected from the group consisting of include imines, amines, oxides, phosphines, ethers, carbonyls, oxazolines, and thioethers.

24. The composition of claim 9 where $R_5$ is a pyridine.

25. The composition of claim 9 where $R_5$ is selected from the group consisting of hydrogen, methyl, ethyl, propyl, butyl, isobutyl, t-butyl, pentyl, hexyl, heptyl, octyl, nonyl, decyl, undecyl, dodecyl, phenyl, benzyl, and all isomers thereof.

26. The composition of claim 9 where $R_2$ and $R_3$ are independently, an alkyl, halogen, benzyl, phenyl, amide, carboxylate, thiolate, hydride or alkoxide group.

27. The composition of claim 9 where $R_2$ and $R_3$ are independently, a $C_1$ to $C_{30}$ alkyl group, a halogen or a phenyl group.

28. The composition of claim 9 where $R_2$ and $R_3$ are independently, a $C_1$ to $C_{30}$ alkyl group.

29. The composition of claim 9 where $R_2$ and $R_3$ are independently, selected from the group consisting of iodine, chlorine, bromine, methyl and benzyl.

30. The composition of claim 9 where $R_2$ and $R_3$ together form a bidentate dianionic ligand.

31. The composition of claim 9 where $R_4$ is hydrogen, or a $C_1$ to $C_{100}$ hydrocarbyl group.

32. The composition of claim 9 where $R_4$ is a $C_1$ to $C_{20}$ alkyl group, or a $C_6$ to $C_{40}$ aromatic group.

33. The composition of claim 9 where $R_4$ is a phenyl group or substituted phenyl group.

34. The composition of claim 9 where $R_4$ is a phenyl group substituted at the 2 and/or 6 positions.

35. The composition of claim 9 where $R_4$ is a phenyl group substituted at the 2, 4, and 6 positions.

36. The composition of claim 9 where $R_4$ is a phenyl group substituted at the 2, 4, and 6 positions with $C_1$ to $C_{40}$ hydrocarbyls.

37. The composition of claim 9 where $R_4$ is a phenyl group substituted at the 2, 4, and 6 positions with groups selected from the group consisting of methyl, ethyl, propyl, isopropyl, butyl, isobutyl, t-butyl, neopentyl, phenyl, and phenyls substituted with $C_1$ to $C_{40}$ hydrocarbyls.

38. The composition of claim 9 where each $R_9$ is, independently, hydrogen, or a hydrocarbyl, a substituted hydrocarbyl, a halocarbyl, or a substituted halocarbyl group, having 1 to 10 carbon atoms.

39. The composition of claim 9 where each $R_9$ is, independently, hydrogen, or a hydrocarbyl, a substituted hydrocarbyl, a halocarbyl, or a substituted halocarbyl group, having 1 to 6 carbon atoms.

40. The composition of claim 9 where each $R_9$ is, independently, hydrogen, or a hydrocarbyl, a substituted hydrocarbyl, a halocarbyl, or a substituted halocarbyl group, having 1, 2 or 3 carbon atoms.

41. The composition of claim 9 where both $R_9$ groups are hydrogen.

42. The composition of claim 9 where $R_{10}$ is, independently, a hydrocarbyl, substituted hydrocarbyl, a halocarbyl, or a substituted halocarbyl group, having 1 to 10 carbon atoms.

43. The composition of claim 9 where $R_{10}$ is independently, a hydrocarbyl, a substituted hydrocarbyl, a halocarbyl, or a substituted halocarbyl group, having 1 to 6 carbon atoms.

44. The composition of claim 9 where $R_{10}$ is independently, a hydrocarbyl, a substituted hydrocarbyl, a halocarbyl, or a substituted halocarbyl group, having 1, 2 or 3 carbon atoms.

45. The composition of claim 9 where the catalyst precursor composition is represented by the following formulae:

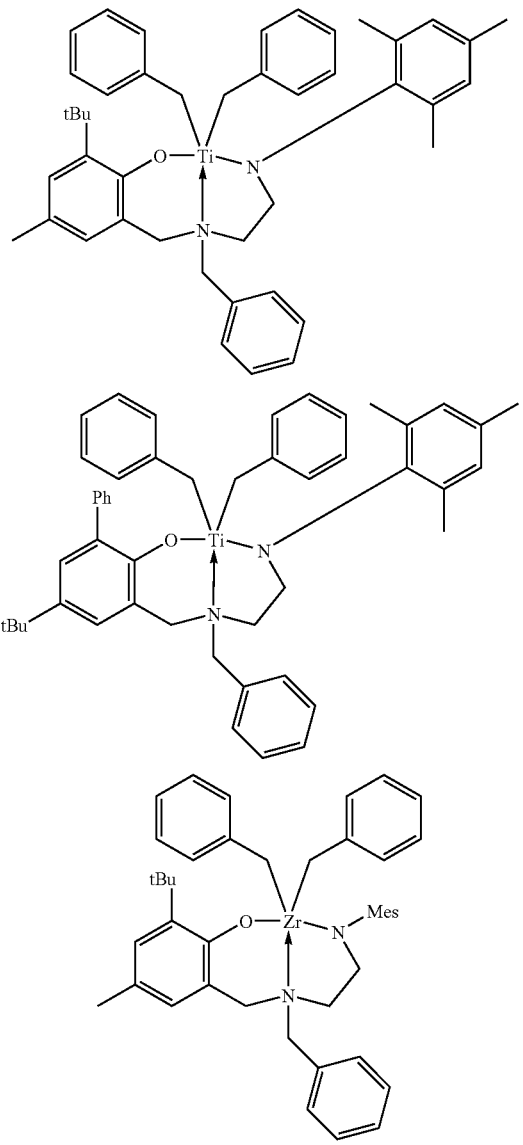

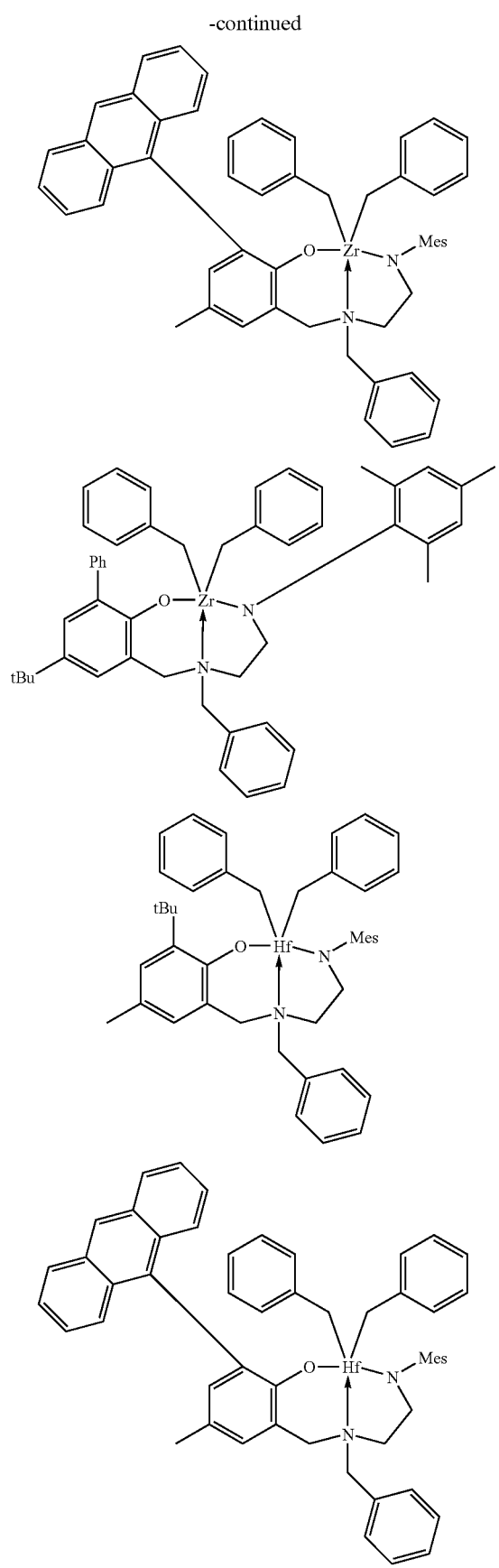
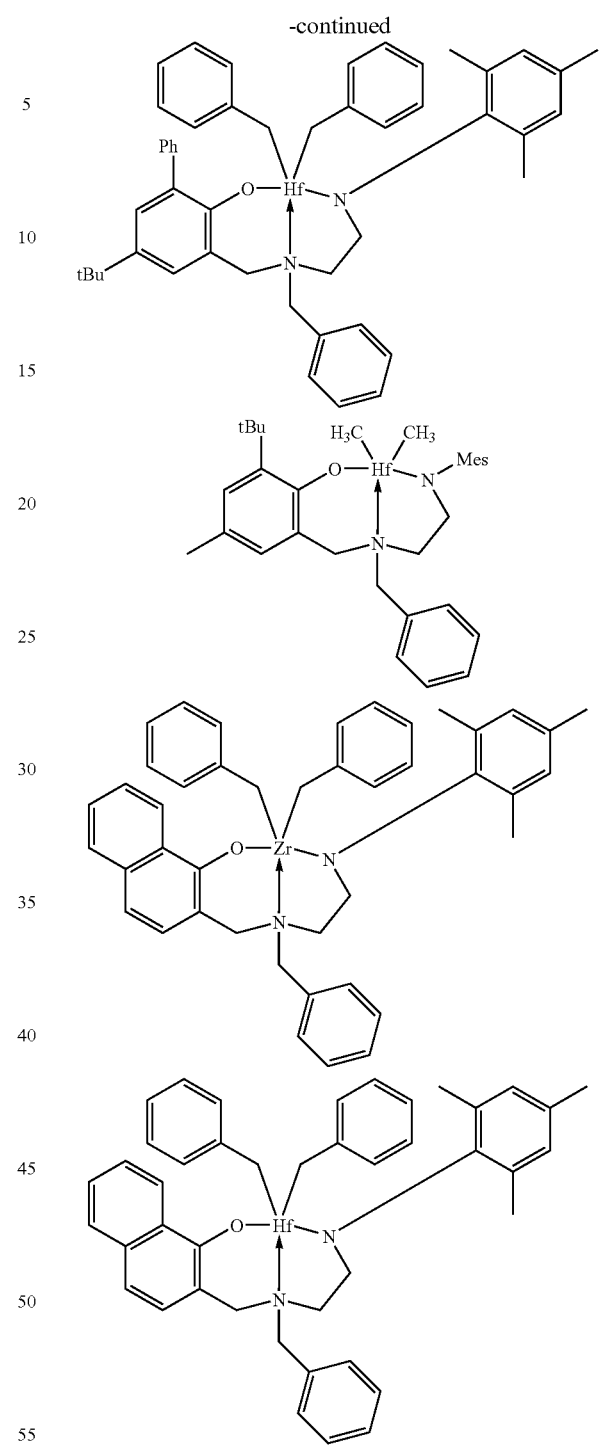

where Mes is mesityl, tBu is tertiary butyl, Ph is phenyl.

46. A catalyst system comprising the composition of claim 9 and an activator.

47. The catalyst system of claim 46 wherein the activator comprises an ionizing activator.

48. The catalyst system of claim 46 wherein the activator comprises a non-coordinating anion.

49. The catalyst system of claim 46 wherein the activator comprises a non-ionizing activator.

50. The catalyst system of claim 46 wherein the activator comprises one or more of:
- methylalumoxane,
- tri(n-butyl)ammonium tetrakis(pentafluorophenyl)borate,
- trisperfluorophenyl boron,
- trisperfluoronapthyl boron,
- trimethylammonium tetraphenylborate,
- triethylammonium tetraphenylborate,
- tripropylammonium tetraphenylborate,
- tri(n-butyl)ammonium tetraphenylborate,
- tri(t-butyl)ammonium tetraphenylborate,
- N,N-dimethylanilinium tetraphenylborate,
- N,N-diethylanilinium tetraphenylborate,
- N,N-dimethyl-(2,4,6-trimethylanilinium)tetraphenylborate,
- trimethylammonium tetrakis(pentafluorophenyl)borate,
- triethylammonium tetrakis(pentafluorophenyl)borate,
- tripropylammonium tetrakis(pentafluorophenyl)borate,
- tri(n-butyl)ammonium tetrakis(pentafluorophenyl)borate,
- tri(sec-butyl)ammonium tetrakis(pentafluorophenyl)borate,
- N,N-dimethylanilinium tetrakis(pentafluorophenyl)borate,
- N,N-diethylanilinium tetrakis(pentafluorophenyl)borate,
- N,N-dimethyl-(2,4,6-trimethylanilinium)tetrakis(pentafluorophenyl)borate,
- trimethylammonium tetrakis-(2,3,4,6-tetrafluorophenylborate,
- triethylammonium tetrakis-(2,3,4,6-tetrafluorophenyl)borate,
- tripropylammonium tetrakis-(2,3,4,6-tetrafluorophenyl)borate,
- tri(n-butyl)ammonium tetrakis-(2,3,4,6-tetrafluoro-phenyl)borate,
- dimethyl(t-butyl)ammonium tetrakis-(2,3,4,6-tetrafluorophenyl)borate,
- N,N-dimethylanilinium tetrakis-(2,3,4,6-tetrafluorophenyl)borate,
- N,N-diethylanilinium tetrakis-(2,3,4,6-tetrafluoro-phenyl)borate,
- N,N-dimethyl-(2,4,6-trimethylanilinium)tetrakis-(2,3,4,6-tetrafluorophenyl)borate;
- di-(i-propyl)ammonium tetrakis(pentafluorophenyl)borate,
- dicyclohexylammonium tetrakis(pentafluorophenyl)borate,
- triphenylphosphonium tetrakis(pentafluorophenyl)borate,
- tri(o-tolyl)phosphonium tetrakis(pentafluorophenyl)borate, and
- tri(2,6-dimethylphenyl)phosphonium tetrakis(pentafluorophenyl)borate.

51. The catalyst system of claim 46 wherein the activator comprises N,N-dimethylanilinium tetra(perfluorophenyl)borate and/or triphenylcarbenium tetra(perfluorophenyl)borate.

52. The catalyst system of claim 46 wherein the activator comprises an alumoxane.

53. A process to polymerize olefins comprising contacting the catalyst system of claim 46 with one or more olefins.

54. A process to polymerize olefins comprising contacting the catalyst system of claim 51 with one or more olefins.

55. A process to polymerize olefins comprising contacting the catalyst system of claim 46 with ethylene.

56. A process to polymerize olefins comprising contacting the catalyst system of claim 51 with ethylene.

57. A process to polymerize olefins comprising contacting the catalyst system of claim 46 with propylene.

58. A process to polymerize olefins comprising contacting one or more $C_2$ to $C_{20}$ alpha olefins with the compound of claim 45 and activator which comprises one or more of:
- alumoxane,
- tri(n-butyl)ammonium tetrakis(pentafluorophenyl)borate,
- trisperfluorophenyl boron,
- trisperfluoronapthyl boron,
- trimethylammonium tetraphenylborate,
- triethylammonium tetraphenylborate,
- tripropylammonium tetraphenylborate,
- tri(n-butyl)ammonium tetraphenylborate,
- tri(t-butyl)arnmonium tetraphenylborate,
- N,N-dimethylanilinium tetraphenylborate,
- N,N-diethylanilinium tetraphenylborate,
- N,N-dimethyl-(2,4,6-trimethylanilinium)tetraphenylborate,
- trimethylammonium tetrakis(pentafluorophenyl)borate,
- triethylammonium tetrakis(pentafluorophenyl)borate,
- tripropylammonium tetrakis(pentafluorophenyl)borate,
- tri(n-butyl)ammonium tetrakis(pentafluorophenyl)borate,
- tri(sec-butyl)ammonium tetrakis(pentafluorophenyl)borate,
- N,N-dimethylanilinium tetrakis(pentafluorophenyl)borate,
- N,N-diethylanilinium tetrakis(pentafluorophenyl)borate,
- N,N-dimethyl-(2,4,6-trimethylanilinium)tetrakis(pentafluorophenyl)borate,
- trimethylammonium tetrakis-(2,3,4,6-tetrafluorophenylborate,
- triethylammonium tetrakis-(2,3,4,6-tetrafluorophenyl)borate,
- tripropylammonium tetrakis-(2,3,4,6-tetrafluorophenyl)borate,
- tri(n-butyl)ammonium tetrakis-(2,3,4,6-tetrafluoro-phenyl)borate,
- dimethyl(t-butyl)ammonium tetrakis-(2,3,4,6-tetrafluorophenyl)borate,
- N,N-dimethylanilinium tetrakis-(2,3,4,6-tetrafluorophenyl)borate,
- N,N-diethylanilinium tetrakis-(2,3,4,6-tetrafluoro-phenyl)borate,
- N,N-dimethyl-(2,4,6-trimethylanilinium)tetrakis-(2,3,4,6-tetrafluorophenyl)borate;
- di-(i-propyl)amrnonium tetrakis(pentafluorophenyl)borate,
- dicyclohexylammonium tetrakis(pentafluorophenyl)borate,
- triphenylphosphonium tetrakis(pentafluorophenyl)borate,
- tri(o-tolyl)phosphonium tetrakis(pentafluorophenyl)borate, and
- tri(2,6-dimethylphenyl)phosphonium tetrakis(pentafluorophenyl)borate.

59. The process of claim 58 where the olefin comprises ethylene.

60. The process of claim 58 where the olefin comprises propylene.

61. The composition of claim 9 where $R_4$ is a halogenated phenyl group.

62. The composition of claim 9 where $R_4$ is a phenyl group substituted at the 2 or 6 positions with a halogen atom.

63. The composition of claim 9 where $R_4$ is a phenyl group substituted at the 2 and 6 positions with a halogen atom.

64. A process to polymerize olefins comprising contacting the catalyst system of claim 51 with ethylene and octene.

\* \* \* \* \*